(12) United States Patent
Faure et al.

(10) Patent No.: US 9,161,917 B2
(45) Date of Patent: Oct. 20, 2015

(54) PROCESS FOR THE PREPARATION OF A SOLID DOSAGE FORM, IN PARTICULAR A TABLET, FOR PHARMACEUTICAL USE AND PROCESS FOR THE PREPARATION OF A PRECURSOR FOR A SOLID DOSAGE FORM, IN PARTICULAR A TABLET

(75) Inventors: Anne Faure, Vosselaar (BE); Jody Firim Marceline Voorspoels, Reninhelst (BE); Roel Jos M. Mertens, Balen (BE); Filip René Irena Kiekens, Geel (BE)

(73) Assignee: GRÜNENTHAL GMBH, Aachen (DE)

( * ) Notice: Subject to any disclaimer, the term of this patent is extended or adjusted under 35 U.S.C. 154(b) by 1133 days.

(21) Appl. No.: 12/916,988

(22) Filed: Nov. 1, 2010

(65) Prior Publication Data

US 2011/0082214 A1    Apr. 7, 2011

Related U.S. Application Data

(63) Continuation of application No. PCT/EP2009/003290, filed on May 8, 2009.

(30) Foreign Application Priority Data

May 9, 2008   (EP) .................................... 08008749

(51) Int. Cl.
*A61K 9/16* (2006.01)
*A61K 9/14* (2006.01)
*A61K 9/20* (2006.01)

(52) U.S. Cl.
CPC ............... *A61K 9/1617* (2013.01); *A61K 9/145* (2013.01); *A61K 9/146* (2013.01); *A61K 9/1641* (2013.01); *A61K 9/1694* (2013.01); *A61K 9/2013* (2013.01); *A61K 9/2031* (2013.01); *A61K 9/2095* (2013.01)

(58) Field of Classification Search
None
See application file for complete search history.

(56) References Cited

U.S. PATENT DOCUMENTS

| | | |
|---|---|---|
| 2,524,855 A | 10/1950 | Schnider et al. |
| 2,806,033 A | 9/1957 | Lewenstein et al. |
| 2,987,445 A | 6/1961 | Levesque |
| 3,652,589 A | 3/1972 | Flick et al. |
| 3,806,603 A | 4/1974 | Gaunt et al. |
| 3,865,108 A | 2/1975 | Hartop |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers |
| 4,343,789 A | 8/1982 | Kawata et al. |
| 4,353,887 A | 10/1982 | Hess |
| 4,404,183 A | 9/1983 | Kawata et al. |
| 4,427,681 A | 1/1984 | Munshi et al. |
| 4,427,778 A | 1/1984 | Zabriskie |
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,485,211 A | 11/1984 | Okamoto |
| 4,529,583 A | 7/1985 | Porter |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura et al. |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |

(Continued)

FOREIGN PATENT DOCUMENTS

| | | |
|---|---|---|
| AR | 46994 | 12/2004 |
| AR | 045353 | 10/2005 |

(Continued)

OTHER PUBLICATIONS

Machine translation for JP 08053331 A (Feb. 1996).*
International Search Report and Written Opinion for Application No. PCT/EP2010/004459 dated Dec. 1, 2010.
International Search Report and Written Opinion for Application No. PCT/EP2013/053894 dated Mar. 22, 2013.
K.H. Bauer, Lehrbuch der Pharmazeutischen Technologie, 6th edition, WVG Stuttgart, 1999.
W.A. Ritschel et al, "Die Tablette", 2nd Edition, Editio Cantor Verlag Aulendorf, 2002.
Tranquilan-Aranilla et al., "Kappa-carrageenan-polyethylene oxide hydrogel blends prepared by gamma irradiation," Radiation Physics and Chemistry vol. 55, pp. 127-131, 1999.
PCT International Search Report and Written Opinion for PCT Application No. PCT/EP2013/057851 dated Jun. 12, 2013.
Application of a modeling system in the formulation of extended release hydrophilic matrices, Reprinted from Pharmaceutical Technology Europe, Jul. 2006.

(Continued)

*Primary Examiner* — Carlos Azpuru
*Assistant Examiner* — Casey Hagopian
(74) *Attorney, Agent, or Firm* — Norris McLaughlin & Marcus, P.A.

(57) ABSTRACT

Process for preparing a powder comprising the steps of providing at least one first component in liquid form at ambient temperature, providing at least one second component having a melting point or melting range in the range from above ambient temperature to below the degradation temperature of said first component, forming a homogenous liquid mixture comprising the at least one first component and the at least one second component by stirring and heating the mixture to or keeping the mixture at a temperature in the range from above the melting point or melting range of the second component and below the degradation temperature of the first component, transferring the liquid mixture to at least one spray congealing unit, spray congealing the mixture, and isolating the powder obtained upon spray congealing.

17 Claims, No Drawings

(56) References Cited

U.S. PATENT DOCUMENTS

| | | |
|---|---|---|
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinity et al. |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,197 A | 4/1993 | Wright et al. |
| 5,211,892 A | 5/1993 | Gueret |
| 5,225,417 A | 7/1993 | Dappen et al. |
| 5,273,758 A | 12/1993 | Royce |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayadshida et al. |
| 5,601,842 A | 2/1997 | Bartholomaeus |
| 5,620,697 A | 4/1997 | Tormala et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Graudums et al. |
| 5,811,126 A | 9/1998 | Krishnamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,228,863 B1 | 5/2001 | Palermo et al. |
| 6,235,825 B1 | 5/2001 | Yoshida et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,326,027 B1 | 12/2001 | Miller et al. |
| 6,337,319 B1 | 1/2002 | Wang |
| 6,340,475 B2 | 1/2002 | Shell et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,387,995 B1 * | 5/2002 | Sojka ............... 524/291 |
| 6,399,100 B1 | 6/2002 | Clancy et al. |
| 6,419,954 B1 | 7/2002 | Chu et al. |
| 6,436,441 B1 | 8/2002 | Sako et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breitenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaeus et al. |
| 7,842,307 B2 | 11/2010 | Oshlack et al. |
| 7,851,482 B2 | 12/2010 | Dung et al. |
| 7,939,543 B2 | 5/2011 | Kupper |
| 7,994,364 B2 | 8/2011 | Fischer et al. |
| 8,075,872 B2 | 12/2011 | Arkenau-Maric et al. |
| 8,101,630 B2 | 1/2012 | Kumar et al. |
| 8,114,383 B2 | 2/2012 | Bartholomaeus et al. |
| 8,114,384 B2 | 2/2012 | Arkenau et al. |
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomaus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Mari et al. |
| 2001/0038852 A1 | 11/2001 | Kolter et al. |

(56) References Cited

U.S. PATENT DOCUMENTS

| | | |
|---|---|---|
| 2002/0012701 A1 | 1/2002 | Kolter et al. |
| 2002/0015730 A1 | 2/2002 | Hoffmann et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0176888 A1 | 11/2002 | Bartholomaeus et al. |
| 2002/0187192 A1 | 12/2002 | Joshi et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0031546 A1 | 2/2003 | Araki et al. |
| 2003/0044458 A1 | 3/2003 | Wright et al. |
| 2003/0044464 A1 | 3/2003 | Zeigler et al. |
| 2003/0064099 A1 | 4/2003 | Oshlack et al. |
| 2003/0068276 A1 | 4/2003 | Hughes et al. |
| 2003/0068370 A1 | 4/2003 | Sackler |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0091630 A1 | 5/2003 | Louie-Helm et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0185105 A1 | 9/2004 | Berner et al. |
| 2004/0213845 A1 | 10/2004 | Sugihara |
| 2004/0213848 A1 | 10/2004 | Li et al. |
| 2005/0015730 A1 | 1/2005 | Gunturi et al. |
| 2005/0031546 A1 | 2/2005 | Bartholomaus et al. |
| 2005/0058706 A1 | 3/2005 | Bartholomaeus et al. |
| 2005/0063214 A1 | 3/2005 | Takashima |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaus |
| 2005/0192333 A1 | 9/2005 | Hinze et al. |
| 2005/0214223 A1 | 9/2005 | Bartholomaeus et al. |
| 2005/0222188 A1 | 10/2005 | Chapman et al. |
| 2005/0236741 A1 | 10/2005 | Arkenau et al. |
| 2005/0245556 A1 | 11/2005 | Brogmann et al. |
| 2005/0266084 A1 | 12/2005 | Li et al. |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedmann et al. |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi et al. |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaus et al. |
| 2006/0193914 A1 | 8/2006 | Ashworth et al. |
| 2006/0194759 A1 | 8/2006 | Eidelson |
| 2006/0194826 A1 | 8/2006 | Oshlack et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0048228 A1 | 3/2007 | Arkenau-Maric et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0259045 A1 | 11/2007 | Mannion et al. |
| 2007/0264327 A1 | 11/2007 | Kumar et al. |
| 2007/0269505 A1 | 11/2007 | Flath et al. |
| 2008/0063725 A1 | 3/2008 | Guimberteau et al. |
| 2008/0069871 A1 | 3/2008 | Vaughn et al. |
| 2008/0081290 A1 | 4/2008 | Wada et al. |
| 2008/0085304 A1 | 4/2008 | Baichwal et al. |
| 2008/0145429 A1 | 6/2008 | Leyenecker et al. |
| 2008/0152595 A1 | 6/2008 | Emigh et al. |
| 2008/0220079 A1 | 9/2008 | Chen et al. |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0280975 A1 | 11/2008 | Badul |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0117191 A1 | 5/2009 | Brown Miller et al. |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0317355 A1 | 12/2009 | Roth et al. |
| 2010/0015223 A1 | 1/2010 | Cailly-Dufestel et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0082214 A1 | 4/2011 | Faure et al. |
| 2011/0092515 A1 | 4/2011 | Qiu et al. |

(56) References Cited

U.S. PATENT DOCUMENTS

| | | | |
|---|---|---|---|
| 2011/0097404 A1 | 4/2011 | Oshlack et al. |
| 2011/0159100 A1 | 6/2011 | Anderson et al. |
| 2011/0187017 A1 | 8/2011 | Haupts |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0225901 A1 | 9/2012 | Leyendecker et al. |
| 2012/0231083 A1 | 9/2012 | Carley et al. |
| 2012/0251637 A1 | 10/2012 | Bartholom us et al. |
| 2013/0028970 A1 | 1/2013 | Schwier et al. |
| 2013/0090349 A1 | 4/2013 | Geibler et al. |
| 2013/0129826 A1 | 5/2013 | Geibler et al. |
| 2013/0209557 A1 | 8/2013 | Barnscheid |
| 2013/0225625 A1 | 8/2013 | Barnscheid et al. |
| 2013/0303623 A1 | 11/2013 | Barnscheid et al. |
| 2014/0094481 A1 | 4/2014 | Fleischer et al. |

FOREIGN PATENT DOCUMENTS

| | | |
|---|---|---|
| AR | 049562 | 8/2006 |
| AR | 053304 | 5/2007 |
| AR | 054222 | 6/2007 |
| AR | 054328 | 6/2007 |
| AU | 2003237944 | 12/2003 |
| AU | 2003274071 | 5/2004 |
| AU | 2003278133 | 5/2004 |
| AU | 2003279317 | 5/2004 |
| AU | 2004264666 | 2/2005 |
| AU | 2004264667 | 2/2005 |
| AU | 2004308653 | 4/2005 |
| AU | 2005259476 | 1/2006 |
| AU | 2005259478 | 1/2006 |
| AU | 2006/210145 B2 | 8/2006 |
| AU | 2006210145 | 8/2006 |
| AU | 2009207796 | 7/2009 |
| AU | 2009243681 | 11/2009 |
| BR | P10413318 | 10/2006 |
| BR | P10413361 | 10/2006 |
| BR | P10513300 | 5/2008 |
| BR | P10606145 | 2/2009 |
| CA | 722109 A | 11/1965 |
| CA | 2082573 | 5/1993 |
| CA | 2577233 A1 | 10/1997 |
| CA | 2650637 A1 | 10/1997 |
| CA | 2317747 | 7/1999 |
| CA | 2343234 A1 | 3/2000 |
| CA | 2352874 | 6/2000 |
| CA | 2414349 A1 | 1/2002 |
| CA | 2456322 A1 | 2/2003 |
| CA | 2502965 A1 | 10/2003 |
| CA | 2502965 | 5/2004 |
| CA | 2503155 A1 | 5/2004 |
| CA | 2534925 | 2/2005 |
| CA | 2534932 | 2/2005 |
| CA | 2489855 A1 | 4/2005 |
| CA | 2551231 | 7/2005 |
| CA | 2572352 | 1/2006 |
| CA | 2572352 A1 | 1/2006 |
| CA | 2572491 | 1/2006 |
| CA | 2572491 A1 | 1/2006 |
| CA | 2595954 | 7/2006 |
| CA | 2229650 C | 8/2006 |
| CA | 2594713 A1 | 8/2006 |
| CA | 2595979 | 8/2006 |
| CA | 2625055 A1 | 4/2007 |
| CA | 2713128 | 7/2009 |
| CA | 2723438 | 11/2009 |
| CA | 2595954 C | 1/2011 |
| CH | 689109 | 10/1998 |
| CL | 20162004 | 5/2005 |
| CL | 20172004 | 5/2005 |
| CL | 200403308 | 9/2005 |
| CL | 200500952 | 11/2005 |
| CL | 200501624 | 12/2005 |
| CL | 200501625 | 6/2006 |
| CN | 87102755 | 10/1987 |
| CN | 87102755 A | 10/1987 |
| CN | 1135175 A | 11/1996 |
| CN | 1473562 A | 2/2004 |
| CN | 1980643 | 4/2005 |
| CN | 101010071 | 6/2005 |
| CN | 1671475 A | 9/2005 |
| CN | 101022787 | 1/2006 |
| CN | 001863513 | 11/2006 |
| CN | 001863514 | 11/2006 |
| CN | 01917862 | 2/2007 |
| CN | 101011395 A | 8/2007 |
| CN | 101027044 | 8/2007 |
| CN | 101057849 A | 10/2007 |
| CN | 101091721 A * | 12/2007 |
| CN | 101111232 | 1/2008 |
| CN | 101175482 | 2/2008 |
| CN | 101394839 A | 3/2009 |
| DE | 2530563 | 1/1977 |
| DE | 4229085 A1 | 3/1994 |
| DE | 4309528 | 9/1994 |
| DE | 4446470 A1 | 6/1996 |
| DE | 69400215 | 10/1996 |
| DE | 19522899 C1 | 12/1996 |
| DE | 2808505 | 1/1997 |
| DE | 19753534 | 6/1999 |
| DE | 19800689 C1 | 7/1999 |
| DE | 19800698 | 7/1999 |
| DE | 19822979 | 12/1999 |
| DE | 69229881 | 12/1999 |
| DE | 19855440 | 6/2000 |
| DE | 19856147 | 6/2000 |
| DE | 19940740 | 3/2001 |
| DE | 19960494 | 6/2001 |
| DE | 10036400 | 6/2002 |
| DE | 69429710 | 8/2002 |
| DE | 10250083 | 12/2003 |
| DE | 10250084 | 5/2004 |
| DE | 10250087 | 5/2004 |
| DE | 10250088 | 5/2004 |
| DE | 10336400 | 3/2005 |
| DE | 10 361 596 | 9/2005 |
| DE | 10 2004 020 220 | 11/2005 |
| DE | 102004019916 | 11/2005 |
| DE | 102004020220 | 11/2005 |
| DE | 10 2004 032 049 | 1/2006 |
| DE | 10 2004 032 051 | 1/2006 |
| DE | 10 2004 032 103 | 1/2006 |
| DE | 10 2005 005 446 | 8/2006 |
| DE | 10 2005 005 449 | 8/2006 |
| DE | 102007011485 | 9/2008 |
| DK | 1658055 | 7/2007 |
| DK | 1658054 | 10/2007 |
| DK | 1515702 | 1/2009 |
| EC | SP066345 | 8/2006 |
| EP | 0008131 | 2/1980 |
| EP | 0216453 | 2/1980 |
| EP | 0043254 A1 | 1/1982 |
| EP | 0008131 B1 | 12/1982 |
| EP | 0177893 | 4/1986 |
| EP | 0216453 A2 | 4/1987 |
| EP | 0226061 | 6/1987 |
| EP | 0228417 | 7/1987 |
| EP | 0229652 A2 | 7/1987 |
| EP | 0232877 | 8/1987 |
| EP | 0240906 A2 | 10/1987 |
| EP | 0 261 616 A | 3/1988 |
| EP | 0261616 A2 | 3/1988 |
| EP | 0270954 | 6/1988 |
| EP | 0277289 | 8/1988 |
| EP | 0293066 | 11/1988 |
| EP | 0261616 A3 | 2/1989 |
| EP | 0328775 | 8/1989 |

(56) References Cited

FOREIGN PATENT DOCUMENTS

| | | |
|---|---|---|
| EP | 0228417 B1 | 8/1990 |
| EP | 0 229 652 B1 | 10/1991 |
| EP | 0229652 B1 | 10/1991 |
| EP | 0 477 135 A | 3/1992 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 | 2/1994 |
| EP | 0598606 | 5/1994 |
| EP | 0636370 A1 | 2/1995 |
| EP | 0641195 A1 | 3/1995 |
| EP | 0647448 A1 | 4/1995 |
| EP | 0654263 A1 | 5/1995 |
| EP | 0661045 | 7/1995 |
| EP | 0675710 A1 | 10/1995 |
| EP | 0682945 | 11/1995 |
| EP | 0693475 | 1/1996 |
| EP | 0820693 | 1/1996 |
| EP | 0696598 | 2/1996 |
| EP | 0216453 B1 | 3/1996 |
| EP | 0583726 B1 | 11/1996 |
| EP | 0756480 A1 | 2/1997 |
| EP | 0760654 A1 | 3/1997 |
| EP | 0780369 | 6/1997 |
| EP | 0785775 A1 | 7/1997 |
| EP | 0 761 211 A1 | 12/1997 |
| EP | 0809488 A1 | 12/1997 |
| EP | 0820698 | 1/1998 |
| EP | 0820753 A2 | 1/1998 |
| EP | 0857062 A2 | 8/1998 |
| EP | 0864324 A1 | 9/1998 |
| EP | 0864326 A2 | 9/1998 |
| EP | 0598606 B1 | 6/1999 |
| EP | 0675710 B1 | 8/1999 |
| EP | 0980894 | 2/2000 |
| EP | 0988106 A1 | 3/2000 |
| EP | 1014941 A1 | 7/2000 |
| EP | 1070504 | 1/2001 |
| EP | 1127871 | 8/2001 |
| EP | 1138321 | 10/2001 |
| EP | 1152026 A1 | 11/2001 |
| EP | 1138321 A3 | 1/2002 |
| EP | 1166776 | 1/2002 |
| EP | 1201233 A1 | 5/2002 |
| EP | 0661045 B1 | 7/2002 |
| EP | 1250045 | 10/2002 |
| EP | 1250045 A2 | 10/2002 |
| EP | 1251120 | 10/2002 |
| EP | 1293127 | 3/2003 |
| EP | 1293195 A1 | 3/2003 |
| EP | 1293196 A2 | 3/2003 |
| EP | 1127871 B1 | 9/2003 |
| EP | 1201233 B1 | 12/2004 |
| EP | 1251120 131 | 12/2004 |
| EP | 1492506 B1 | 1/2005 |
| EP | 1166776 B1 | 2/2005 |
| EP | 1502592 A1 | 2/2005 |
| EP | 1658055 | 2/2005 |
| EP | 1515702 | 3/2005 |
| EP | 1527775 A1 | 4/2005 |
| EP | 1558221 A1 | 8/2005 |
| EP | 1558257 | 8/2005 |
| EP | 1560585 | 8/2005 |
| EP | 1611880 A2 | 1/2006 |
| EP | 1658054 | 5/2006 |
| EP | 1138321 B1 | 1/2007 |
| EP | 1740161 | 1/2007 |
| EP | 1658055 B1 | 3/2007 |
| EP | 1765303 | 3/2007 |
| EP | 1786403 | 5/2007 |
| EP | 1558221 B1 | 6/2007 |
| EP | 1658054 B1 | 6/2007 |
| EP | 1842533 A2 | 10/2007 |
| EP | 1845955 | 10/2007 |
| EP | 1845956 | 10/2007 |
| EP | 1859789 | 11/2007 |
| EP | 1980245 A1 | 10/2008 |
| EP | 1897545 | 12/2008 |
| EP | 2131830 | 12/2009 |
| EP | 2246063 A1 | 11/2010 |
| EP | 2249811 | 11/2010 |
| EP | 2273983 | 1/2011 |
| EP | 2402004 A2 | 1/2012 |
| ES | 2336571 | 12/2004 |
| ES | 2260042 | 11/2006 |
| ES | 2285497 | 11/2007 |
| ES | 2288621 | 1/2008 |
| ES | 2289542 | 2/2008 |
| ES | 2315505 | 4/2009 |
| GB | 1 147 210 | 4/1969 |
| GB | 1147210 A | 4/1969 |
| GB | 1567727 | 5/1980 |
| GB | 2047095 A | 11/1980 |
| GB | 2057878 | 4/1981 |
| GB | 2238478 A | 6/1991 |
| HR | P20070272 | 6/2007 |
| HR | 20070456 | 11/2007 |
| JP | S36-022895 | 11/1961 |
| JP | S55162714 A | 12/1980 |
| JP | S5659708 A | 5/1981 |
| JP | S56169622 A | 12/1981 |
| JP | S62240061 A | 10/1987 |
| JP | H0249719 A | 2/1990 |
| JP | 03-501737 A | 4/1991 |
| JP | 08053331 A * | 2/1996 |
| JP | 8-505076 A | 6/1996 |
| JP | H09508410 A | 8/1997 |
| JP | H1057450 A | 3/1998 |
| JP | 2002524150 A | 8/2002 |
| JP | 2002-275175 | 9/2002 |
| JP | 2003125706 A | 5/2003 |
| JP | 2003526598 A | 9/2003 |
| JP | 2005-314407 A | 11/2005 |
| JP | 2005534664 | 11/2005 |
| JP | 2007501201 A | 1/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009531453 A | 9/2009 |
| KR | 1020060069832 | 6/2006 |
| KR | 20070039041 | 4/2007 |
| KR | 20070111510 | 11/2007 |
| KR | 20090085312 A | 8/2009 |
| KR | 20100111303 | 10/2010 |
| KR | 20110016921 | 2/2011 |
| MX | 2007000008 | 3/2007 |
| MX | 2007000009 | 3/2007 |
| MX | 2007009393 | 8/2007 |
| MX | 2010008138 | 8/2010 |
| MX | 2010012039 | 11/2010 |
| NO | 20061054 | 3/2006 |
| NO | 20070578 | 1/2007 |
| NO | 20074412 | 11/2007 |
| PT | 1699440 | 12/2004 |
| PT | 1658054 | 5/2006 |
| PT | 1658055 | 7/2007 |
| PT | 1515702 | 12/2008 |
| RU | 2131244 | 6/1999 |
| RU | 2198197 C2 | 2/2003 |
| RU | 2396944 C2 | 7/2004 |
| RU | 2326654 C2 | 9/2005 |
| RU | 2354357 | 12/2007 |
| RU | 2007103712 | 9/2008 |
| RU | 2007103707 | 11/2008 |
| RU | 2007132975 | 4/2009 |
| SI | 1515702 | 4/2009 |
| SI | 1699440 | 11/2009 |
| TW | I254634 B | 5/2006 |
| WO | 8000841 | 5/1980 |
| WO | 89/05624 | 6/1989 |

(56) References Cited

FOREIGN PATENT DOCUMENTS

| | | |
|---|---|---|
| WO | 90/03776 | 4/1990 |
| WO | 90/03776 A1 | 4/1990 |
| WO | 93/06723 | 4/1993 |
| WO | 93/10758 | 6/1993 |
| WO | 93/11749 | 6/1993 |
| WO | 93 23017 | 11/1993 |
| WO | 93/23017 A1 | 11/1993 |
| WO | 94/06414 | 3/1994 |
| WO | 94/08567 | 4/1994 |
| WO | 95/17174 | 6/1995 |
| WO | 95/17174 A1 | 6/1995 |
| WO | 95/20947 | 8/1995 |
| WO | 95/22319 | 8/1995 |
| WO | WO 95/20947 A1 | 8/1995 |
| WO | 95/30422 | 11/1995 |
| WO | 96/00066 | 1/1996 |
| WO | 96/03979 | 2/1996 |
| WO | 96/03979 A1 | 2/1996 |
| WO | 96/14058 | 5/1996 |
| WO | WO 97/00673 A1 | 1/1997 |
| WO | 97/33566 | 9/1997 |
| WO | 9749384 | 12/1997 |
| WO | 9835655 A3 | 2/1998 |
| WO | 98/20073 | 5/1998 |
| WO | 98/28698 | 7/1998 |
| WO | 98/35655 | 8/1998 |
| WO | 98/35655 A2 | 8/1998 |
| WO | WO 98/51758 A1 | 11/1998 |
| WO | 99/12864 | 3/1999 |
| WO | 99/12864 A1 | 3/1999 |
| WO | 99/32120 | 7/1999 |
| WO | 99/44591 | 9/1999 |
| WO | 99/48481 | 9/1999 |
| WO | WO 99/45887 A2 | 9/1999 |
| WO | WO 00/13647 A1 | 3/2000 |
| WO | 00/33835 | 6/2000 |
| WO | 00/40205 | 7/2000 |
| WO | 01/08661 | 2/2001 |
| WO | 01/12230 | 2/2001 |
| WO | 01/15667 | 3/2001 |
| WO | 01/52651 | 7/2001 |
| WO | WO 01/58451 A1 | 8/2001 |
| WO | 01/97783 | 12/2001 |
| WO | 02/26061 | 4/2002 |
| WO | 02/26262 | 4/2002 |
| WO | 02/26928 | 4/2002 |
| WO | 0235991 A2 | 5/2002 |
| WO | 02/071860 A | 9/2002 |
| WO | 02/088217 A1 | 11/2002 |
| WO | WO 02/094254 A2 | 11/2002 |
| WO | 03/006723 | 1/2003 |
| WO | 03/013476 | 2/2003 |
| WO | 03/013479 | 2/2003 |
| WO | 03/015531 | 2/2003 |
| WO | WO 03/013538 A1 | 2/2003 |
| WO | 03/024430 | 3/2003 |
| WO | 03024426 A1 | 3/2003 |
| WO | WO 03/018015 A1 | 3/2003 |
| WO | 03/026624 A1 | 4/2003 |
| WO | 03/028698 | 4/2003 |
| WO | 03/028990 A1 | 4/2003 |
| WO | 03/031546 | 4/2003 |
| WO | 03026743 A2 | 4/2003 |
| WO | 03/035029 | 5/2003 |
| WO | 03/035053 | 5/2003 |
| WO | 03/035054 | 5/2003 |
| WO | 03/035177 A2 | 5/2003 |
| WO | WO 03/039561 A1 | 5/2003 |
| WO | WO 03/049689 A2 | 6/2003 |
| WO | 03/053417 | 7/2003 |
| WO | 03/068392 | 8/2003 |
| WO | WO 03/070191 A1 | 8/2003 |
| WO | 03/092648 A1 | 11/2003 |
| WO | 03/094812 | 11/2003 |
| WO | 03/105808 | 12/2003 |
| WO | 2004/004693 A1 | 1/2004 |
| WO | 2004/043967 | 2/2004 |
| WO | 2004/026262 | 4/2004 |
| WO | 2004/026263 | 4/2004 |
| WO | WO 2004/026280 A2 | 4/2004 |
| WO | 2004/037230 | 5/2004 |
| WO | 2004/037259 | 5/2004 |
| WO | 2004/037260 | 5/2004 |
| WO | 2004/066910 A2 | 8/2004 |
| WO | WO 2004/078212 A1 | 9/2004 |
| WO | 2004/084869 A1 | 10/2004 |
| WO | 2004/093801 A2 | 11/2004 |
| WO | 2004/093819 | 11/2004 |
| WO | 2004 098567 A2 | 11/2004 |
| WO | 2004/100894 A2 | 11/2004 |
| WO | 2005/016313 | 2/2005 |
| WO | 2005/016314 | 2/2005 |
| WO | 2005/032524 A2 | 4/2005 |
| WO | 2005/065646 A2 | 4/2005 |
| WO | 2005/041968 | 5/2005 |
| WO | 2005/053587 A1 | 6/2005 |
| WO | 2005/053656 | 6/2005 |
| WO | 2005/053656 A1 | 6/2005 |
| WO | 2005/055981 A2 | 6/2005 |
| WO | 2005053587 A1 | 6/2005 |
| WO | 2005/063214 | 7/2005 |
| WO | 2005/066183 | 7/2005 |
| WO | WO 2005/060942 A1 | 7/2005 |
| WO | 2005079760 A1 | 9/2005 |
| WO | 2005/102286 | 11/2005 |
| WO | 2005105036 A1 | 11/2005 |
| WO | WO 2005/102294 A2 | 11/2005 |
| WO | 2006/002883 | 1/2006 |
| WO | 2006/002884 | 1/2006 |
| WO | 2006/002886 | 1/2006 |
| WO | 2006002884 | 1/2006 |
| WO | WO 2006/002884 B1 | 3/2006 |
| WO | WO 2006/039692 A2 | 4/2006 |
| WO | 2005102294 | 5/2006 |
| WO | 2006058249 A2 | 6/2006 |
| WO | 2006/082097 | 8/2006 |
| WO | 2006/082099 | 8/2006 |
| WO | WO 2006/105615 A1 | 10/2006 |
| WO | WO 2006/128471 A2 | 12/2006 |
| WO | 2007/005716 A2 | 1/2007 |
| WO | 2007/008752 | 1/2007 |
| WO | WO 2007/014061 A2 | 2/2007 |
| WO | 2007/045462 A2 | 4/2007 |
| WO | 2007/048233 | 5/2007 |
| WO | 2007/053698 | 5/2007 |
| WO | 2007/045462 A3 | 6/2007 |
| WO | 2007/085024 A2 | 7/2007 |
| WO | 2007085024 A2 | 7/2007 |
| WO | 2007085024 A3 | 7/2007 |
| WO | 2007 103286 | 9/2007 |
| WO | 2007103105 A2 | 9/2007 |
| WO | 2007/112285 | 10/2007 |
| WO | WO 2007/112286 A2 | 10/2007 |
| WO | WO 2007/131357 A1 | 11/2007 |
| WO | 2008 023261 A1 | 2/2008 |
| WO | 2008033523 A1 | 3/2008 |
| WO | WO 2008/069941 A2 | 6/2008 |
| WO | 2008/086804 A2 | 7/2008 |
| WO | 2008/107149 A2 | 9/2008 |
| WO | 2008107149 | 9/2008 |
| WO | 2008107149 A2 | 9/2008 |
| WO | 2008107149 A3 | 9/2008 |
| WO | WO2008/132707 A1 | 11/2008 |
| WO | WO 2008/142627 A2 | 11/2008 |
| WO | 2008/148798 A2 | 12/2008 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | 2009/092601 A1 | 7/2009 |
| WO | 2009092601 | 7/2009 |

(56) References Cited

FOREIGN PATENT DOCUMENTS

| | | | |
|---|---|---|---|
| WO | 2009112273 A2 | 9/2009 | |
| WO | WO 2009/110005 A2 | 9/2009 | |
| WO | 2009/135680 A1 | 11/2009 | |
| WO | 2009135680 | 11/2009 | |
| WO | WO 2010/022193 A2 | 2/2010 | |
| WO | WO 2010/044842 A1 | 4/2010 | |
| WO | 2010057036 A2 | 5/2010 | |
| WO | WO 2010/066034 A1 | 6/2010 | |
| WO | WO 2010/083843 A1 | 7/2010 | |
| WO | WO 2010/083894 A1 | 7/2010 | |
| WO | WO 2010/088911 A1 | 8/2010 | |
| WO | WO 2010/105672 A1 | 9/2010 | |
| WO | 2010140007 A2 | 12/2010 | |
| WO | 2010140007 A9 | 12/2010 | |
| WO | WO 2010/149169 A2 | 12/2010 | |
| WO | 2011009602 | 1/2011 | |
| WO | 2011009603 | 1/2011 | |
| WO | 2011009604 | 1/2011 | |
| WO | 2011095314 A3 | 8/2011 | |
| WO | 2011/109441 A1 | 9/2011 | |
| WO | WO 2011/128630 A2 | 10/2011 | |
| WO | 2012028317 A1 | 3/2012 | |
| WO | 2012028318 A1 | 3/2012 | |
| WO | WO 2012/028319 A1 | 3/2012 | |
| WO | WO 2012/119727 A1 | 9/2012 | |
| WO | WO 2012/166474 A1 | 12/2012 | |
| WO | WO 2013/003845 A1 | 1/2013 | |
| WO | WO 2013/017234 A1 | 2/2013 | |
| WO | WO 2013/084059 A1 | 6/2013 | |
| WO | WO 2014/059512 A1 | 4/2014 | |

OTHER PUBLICATIONS

Application of Opadry II, complete film coating system, on metformin HCl extended release matrices containing Polyox water soluble resin, Colorcon Apr. 2009.
Evaluation of Verapamil HCl (240 mg) Extended Release Matrix Formulation Using USP Apparatus III in Biorelevant Dissolution Media, Jul. 2009.
Formulation of Polyox ER Matrices for a Highly Soluble Active, Colorcon Jul. 2009.
Investigation of a Directly Compressible Metformin HCl 500mg Extended Release Formulation Based on Hypromellose, Colorcon Jul. 2009.
Metformin Hydrochloride 750 mg Extended Release Tablets, Lubrizol Advanced Materials, Inc., Sep. 2010.
Metformin Hydrochloride1000 mg Extended Release Tablets, Lubrizol Advanced Materials, Inc., Nov. 20, 2009, Previous Edition Dec. 19, 2008.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Physico-mechanical Characterization of Polyox for Table Manufacture, Colorcon Jul. 2009.
Tramadol Hydrochloride 100 mg Extended Release Tablets, Lubrizol Advanced Materials, Inc., Sep. 2010.
Katz et al., Clin. J. Pain, 23(8): 648-660 (2007).
Arnold, "Teen Abuse of Painkiller OxyContin on the Rise," www.npr.org, Dec. 19, 2005.
Baum et al., Public Health Reports, 102(4): 426-429 (1987).
Purdue News, "Purdue Pharma Provides Update on Development of New Abuse-Resistant Pain Medications; FDA Cites Patient Needs As First Priority; New Drug Application Delayed," www.headaches.about.com, Jun. 18, 2002.
Strang, British Med. J., 302: 969 (1991).
Tompkins et al., Psychopharma., 210: 471-480 (2010).
Waters et al., Am. J. Psychiatry, 164(1): pp. 173-174 (2007).
Tablet, www.docstoc.com (2011).
Dachille, F. et al., "High-Pressure Phase Transformation in Laboratory Mechanical Mixers and Mortars", 1906., Nature, 186, pp. 1-2 (abstract).
Conversion of 18.8 kiloponds to newtons, http://www.unitconversion.org/force/newtons-to-kiloponds-conversion.html on Jul. 5, 2011.
Waltimo et al. A novel bite force recorder and maximal isometric bite force values for healthy young adults. Scand J Dent Res. 1993, vol. 101, pp. 171-175.
Waltimo et al. Maximal bite force and its association with signs and symptoms of crandiomandibular disorders in young Finnish non-patients. Acta Odonol. Scand. 1995, vol. 53, pp. 254-258.
Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.
Augustine, R.L., Catalytic Hydrogenation of a, B-Unsaturated Ketones. III The Effect of Quantity and Type of Catalysts, J.Org Chem. 28(1), pp. 152-155, Abstract 1963.
Goodman and Gilman, "The Pharmacological Basis of Therapeutics, Seventh Edition", MacMillan Publishing Company, Table of Contents. 1985.
McGinity et al., Hot-Melt Extrusion as a Pharmaceutical Process, American Pharmaceutical Review, vol. 4 (2), pp. 25-36, 2001.
Weiss, U., "Derivatives of Morphine. I 14-Dihydroxydihydromorphinone," J. Am. Chem. Soc. 77, pp. 5891-5892, Nov. 20, 1955.
European Search Report, Application No./Patent No. 11006253.6-2112, Dec. 16, 2011.
European Search Report, Application No./Patent No. 11006254.4-2112, Dec. 16, 2011.
European Search Report, Application No./Patent No. 11008131.2-1219, Feb. 24, 2012.
European Search Report, Application No./Patent No. 12001296.8-1219, Jun. 26, 2012.
European Search Report, Application No./Patent No. 11009129.5-2112, Apr. 10, 2012.
European Search Report, Application No./Patent No. 12001301.6-1219, Jun. 26, 2012.
A. James, "The legal and clinical implications of crushing tablet medication", Nurse Times 100(50), 28-33, 2004.
C. W. McGary, Jr. "Degradation of Poly(ethylene Oxide)", Journal of Polymer Science vol. XLVI,1960, pp. 51-57.
P. Cornish "Avoid the Crush": hazards of medication administration in patients with dysphagia or a feeding tube, CMA Media Inc., CMAJ. 172(7), pp. 871-872, 2005.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
Griffin, "Classification of Surface-Active Agents by HLB" Journal of the Society of Cosmetic Chemists, Atlas Powder Company, 1949, pp. 311-326.
Griffith et al. "Tablet Crushing and the Law: The Implications for Nursing" Professional Nurse 19(1), pp. 41-42, 2003.
Mitchell, "Oral Dosage Forms That Should Not Be Crushed: 2000 Update" Hospital Pharmacy 35(5), 553-557, 2000.
Munjal et al."Polymeric Systems for Amorphous Delta9-Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Ozeki et al. "Control of Medicine Release From Solid Dispersion Through Poly(ethylene oxde)-Carboxyvinylpolymer Interaction", International Journal of Pharmaceutics, 165, 1998, pp. 239-244.
Ozeki et al. "Controlled Release From Solid Dispersion Composed of Poly(ethylene oxide)-Carbopol Interpolymer Complex With Various Cross-Linking Degrees of Carbopol", Journal of Controlled Release. 63, 2000. pp. 287-295.
Munsell Color Company, "The Munsell Book of Color: Glossy Collection", X-Rite, Originally published in 1966, pp. 1-7.
Schier et al. "Fatality from Administration of Labetalol and Crushed Extended-Release Nifedipine" The Annals of Pharmacotherapy vol. 37, 1420-1423, Oct. 2003.
"The Dissolution Procedure: Development and Validation", heading "Study Design", "Time Points" US Pharmacopoeia (USP), General Chapter 1092, pp. 1-15, 2006.

(56) References Cited

OTHER PUBLICATIONS

Wade and Weller, "Handbook of Pharmaceutical Excipients: 2nd Edition", The American Pharmaceutical Association and the Pharmaceutical Press, Table of Contents pp. v-vi, 1994.
PCT International Search Report and Written Opinion for PCT Application No. PCT/EP2013/059728 dated Aug. 6, 2013.
PCT International Search Report and Written Opinion for PCT Application No. PCT/EP2009/003290 dated Jul. 9, 2009.
"Polyox water soluble resins" 2003. http://www.dow.com/webapps/lit/litorder.asp?filepath=polyox/pdfs/noreg/326-00002.pdf.
Dachille, F. et al., "High-Pressure Phase Transformation in Laboratory Mechanical Mixers and Mortars", 1960., Nature, 186, pp. 1-2 (abstract).
Maggi, L. et al., "High molecular weight polyethylene oxides (PEOs) as an alternative to HPMC in controlled release dosage form", 2000, International Journal of Pharmaceutics, 195 pp. 229-238.
Freed et al. pH control of nucleophilic/electrophilic oxidation. International Journal of Pharmaceutics. 2008, vol. 357, pp. 180-188.
Waterman et al. Stabilization of Pharmaceuticals to Oxidative Degradation. Pharmaceutical Development and Technology. 2002, vol. 7, No. 1, pp. 1-32.
Handbuch der Kunststoff-Extrusionstechnik 1, "Grundlagen" in Chapter 1.2 "Klassifizierung von Extrudern", pp. 3-7. 1989.
2.9 Methoden der pharmazeutischen Technologie 143-144, 1997.
Maggi. Therapeutic Potential of Capsaicin-like Molecules. 1Life Sciences, vol. 51, pp. 1777-1781, 1992.
European Search Report and Written Opinion for EP Application No. 13197503.9-1460, Feb. 18, 2014.
European Search Report and Written Opinion for EP Application No. 13176309.9-1460, Oct. 9, 2013.
Gryczke et al, "Development and evaluation of orally disintegrating tablets (ODTs) containing Ibuprofen granules prepared by hot melt extrusion", Colloids and surfaces., B: Biointerfaces, Elsevier, Amsteram, NL, vol. 86, No. 2, Apr. 5, 2011, pp. 275-284.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
European Search Report and Written Opinion for EP Application No. 13425151.1-1460, Mar. 11, 2014.
PCT Second Written Opinion for PCT Application No. PCT/EP2013/057851 dated Apr. 15, 2014.
Polyox, Colorcon, Application Data (Apr. 2009) downloaded from http://www.colorcon.com/literature/marketing/mr/Extended%20Release/POLYOX/English/ads_PEO_Antioxidant.pdf.
Rowe et al. Handbook of Pharmaceutical Excipients. Sixth Edition. 2009, pp. v-ix, Table of Contents.
Brown, "The Dissolution Procedure: Development and Validation" vol. 31(5). Chapter 1092, 2006, pp. 1-15.
Cawello, "Parameters for Compartment-free Pharmacokinetics—Standardization of Study Design, Data Analysis and Reporting" 1999, pp. XI-XIII (table of contents).
Hoepfner et al. Fiedler Encyclopedia of Excipients. 2007, Table of Contents only.
Hong et al. Dissolution kinetics and physical characterization of three-layered tablet with poly(ethylene oxide) core matrix capped by Carbopol. Int .J. Pharmacol. 2008, vol. 356, pp. 121-129.
European Pharmacopoeia, Third Edition, Council of Europe, Strasbourg, 1997, pp. 127-152.
European Pharmacopoeia, Third Edition Supplement 2000, Council of Europe, Strasbourg, 2000, pp. 85-107.
Tikhonov, A. et al., Biopharmacy. The Manual for Students of Pharmaceutical Universities and Departments. 2003, pp. 40-41, Kharkov, Ukraine. (Full English translation attached.).
Bauer, et al. Lehrbuch der Pharmazeutischen Technologie. Eight Edition 2006. Stuttgart, pp. 343-352.
Hartauer, Pharma. Dev. & Tech, 5 (3) 303-310 (2000).
Marques; Tablet breaking force. 2008.

Ritschel et al. Die Tablette: Handbuch der Entwicklung. Herstellung und Qualitatssicherung. 2nd Edition, 2002, Ch 6, pp. 69-82 and 115-136.
Ritschel et al. Die Tablette: Handbuch der Entwicklung, Herstellung und Qualitatssicherung. 2nd Edition, 2002, Table of content.
Wagner, Pharmazeutische Biologie—Drogen und ihre Inhaltsstoffe—Scharfstoffdrogen. 2nd., revised edition. Gustav Fischer Verlag, Stuttgart—N.Y., 1982,Table of Content.
Zeeshan. F and N. Bukhari, "Development and Evaluation of a Novel Modified-Release Pellet-Based-Tablet System for the Delivery of Loratadine and Pseudophedrine Hydrochloride as Model Drugs," AAPS PharmaSciTech 11(2); 910-916 (available on-line May 22, 2010).
Polyox water-soluble resins (DOW Mar. 2002): see http://msds-search.dow.com/PublishedLiteratureDOWCOM/dh_0031/0901b8038003 1a4a.pdf?filepath=/326-00001.pdf &fromPage=GetDoc).
Swarbrick, Encyclopedia of Pharmaceutical Technology. Informa Healthcare, 1988, 1st edition, vol. 1, table of contents.
Swarbrick, Encyclopedia of Pharmaceutical Technology. Informa Healthcare, 1988, 1st edition, vol. 2, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 20, table of contents.
PCT Second Written Opinion for PCT Application No. PCT/EP2013/053893 dated Feb. 21, 2014.
Yeh et al., Stability of Morphine in Aqueous Solution III: Kinetics of Morphine Degradation in Aqueous Solution, Wiley Subscription Services, Inc., Journal of Pharmaceutical Sciences, 50(1): 35-42 (1961).
Almeida, A. et al., Ethylene vinyl acetate as matrix for oral sustained release dosage forms produced via hot-melt extrusion, European Journal of Pharmaceutics and Biopharmaceutics 77 (2011) 297-305.
Almeida, A. et al., Sustained release from hot-melt extruded matrices based on ethylene vinyl acetate and polyethylene oxide, European Journal of Pharmaceutics and Biopharmaceutics 82 (2012) 526-533.
Sreenivasa, B. et al, Design and evaluation of ethylene vinyl acetate sintered matrix tablets, Indian Journal of Pharmaceutical Sciences, Sep.-Oct. 2003, 65(5): 496-502.
European Search Report and Written Opinion for EP Application No. 13169658.5, Aug. 6, 2013.
European Search Report and Written Opinion for EP Application No. 13169659.3, Aug. 6, 2013.

(56) References Cited

OTHER PUBLICATIONS

Foye, W., Principles of Medicinal Chemistry; Structural Features and Pharmacologic Activity, pp. 63-66 at 65 (1989).
Foye, W., Principles of Medicinal Chemistry; Analgesics pp. 241-242, at 241 (1989).
Remington, The Science and Practice of Pharmacy, 19th ed., vol. II, p. 1457 (1995) (providing a table of DFA-approved commercially marketed salts).
Spassov et al., Stereochemistry of Diastereomeric 3-Dialkylaminopropanols and O-Derivatives, J.f. prakt. Chemie, 323:5, 793-800 (1981).
PCT International Search Report and Written Opinion for PCT Application No. PCT/EP2014/064830 dated Aug. 6, 2014.
Lenindzer, A., "The molecular basis of the structure and functions of cells" Moscow 1974, p. 68.
Kondrat, T. , "Technology dosage forms" Moscow 1991, p. 96.
Wu et al. Mathematical modeling and in vitro study of controlled drug release via a highly swellable and dissoluble polymer matrix: polyethylene oxide with high molecular weights. Journal of Controlled Release. 2005. vol. 102, pp. 569-581.
Ravin, Louis. Preformulation. Chapter 76. In Remington's Pharmaceutical Sciences, 17th Ed, 1985.
Disanto, Anthony. Bioavailability and Bioequivalency Testing. Chapter 77. In Remington's Pharmaceutical Sciences, 17th Ed, 1985.
Knevel, Adelbert. Separation. Chapter 78. In Remington's Pharmaceutical Sciences, 17th Ed, 1985.
Phillips, G. Briggs. Sterilization. Chapter 79. In Remington's Pharmaceutical Sciences, 17th Ed, 1985.
Siegel, Frederick. Tonicity, Osmoticity, Osmolality, and Osmolarity. Chapter 80. In Remington's Pharmaceutical Sciences, 17th Ed, 1985.
Giles et al. Plastic Packaging Materials. Chapter 81. In Remington's Pharmaceutical Sciences, 17th Ed, 1985.
Lintner, Carl. Stability of Pharmaceutical Products. Chapter 82. In Remington's Pharmaceutical Sciences, 17th Ed, 1985.
Erskine, Jr., Clyde. Quality Assurance and Control. Chapter 83. In Remington's Pharmaceutical Sciences, 17th Ed, 1985.
Nairn, J.G., Solutions, Emulsion, Suspensions and Extractives. Chapter 84. In Remington's Pharmaceutical Sciences, 17th Ed, 1985.
Avis, Kenneth. Parenteral Preparations. Chapter 85. In Remington's Pharmaceutical Sciences, 17th Ed, 1985.
Turco et al. Intravenous Admixtures. Chapter 86. In Remington's Pharmaceutical Sciences, 17th Ed, 1985.
Mullins, John. Ophthalmic Preparations. Chapter 87. In Remington's Pharmaceutical Sciences, 17th Ed, 1985.
Block, Lawrence. Medicated Applications. Chapter 88. In Remington's Pharmaceutical Sciences, 17th Ed, 1985.
Rippie, Edward. Powders. Chapter 89. In Remington's Pharmaceutical Sciences, 17th Ed, 1985.
King et al. Oral Solid Dosage Forms. Chapter 90. In Remington's Pharmaceutical Sciences, 17th Ed, 1985.
Porter, Stuart. Coating of Pharmaceutical Dosage Forms. Chapter 91. In Remington's Pharmaceutical Sciences, 17th Ed, 1985.
Longer et al. Sustained-Release Drug Delivery Systems. Chapter 92. In Remington's Pharmaceutical Sciences, 17th Ed, 1985.
Sciarra et al. Aerosols. Chapter 93. In Remington's Pharmaceutical Sciences, 17th Ed, 1985.
International Search Report, dated Jul. 9, 2009.
International Preliminary Report on Patentability, dated Aug. 19, 2010.
CARBOPOL 71G, retrieved Mar. 10, 2014 from http://www.lubrizol.com/LifeScience/Products/Carbopol71G-NF.html.
POLYOX WSR-303, retrieved Mar. 10, 2014 from URL http://www.dow.com/dowwolff/en/industrial_solutions/polymers/polyethylene.
Kalant et al., Death in Amphetamine Users: Causes and Rates, CMA Journal, vol. 112, Feb. 8, 1975 pp. 299-304.
Deighan, C.J. et al., Rhabdomyolysis and acute renal failure resulting from alcohol and drug abuse, Q.J Med, vol. 93, 2000, pp. 29-33.
Woodburn, K.R., Vascular complications of injecting drug misuse, Br. J. of Surgery, vol. 83, 1996, pp. 1329-1334.

Dow Chemical Company, Dow Excipients for Controlled Release of Drugs in Hydrophilic Matrix Systems, 2006, pp. 1-36.
Sax et al., Hawley's Condensed Chemical Dictionary, 11th ed., 1987, p. 1233, definition of "wax".
Riippi et al., The effect of compression force on surface structure, crushing strength, friability and disintegration time of erythromycin acistrate tablets, Eur J Pharm Biopharm, vol. 46, 1998, pp. 339-345.
Goodman and Gilman, "The Pharmacological Basis of Therapeutics, Seventh Edttion", MacMillan Publishing Company, Chapter 22, pp. 491-530. 1985.
Goodman and Gilman. "The Pharmacological Basis of Therapeutics, Seventh Edttion", MacMillan Publishing Company, Chapter 23, pp. 533-579. 1985.
Rowe et al., Handbook of Pharmaceutical Excipients, Seventh Edition, 2012, Table of Contents.
Costa et al., Eur. J. Pharni. Sci. 2001, 13(2), 123-133.
Encyclopedia of Pharmaceutical Technology, informa Healthcare, $1^{st}$ Edition, 1996, Table of Contents,.
Note for Guidance on Stability Testing, EMEA, Aug. 2003, pp. 1-20.
Repka MA,Drug Dev Ind Pharm. Oct. 2007;33(10):1043-57. (Abstract).
Kurt H. Bauer, K. Lehmann, Hermann P. Osterwald, Rothgang, Gerhart, 1st edition, 1998, Medpharm Scientific Publishers (table of contents).
O.G. Piringer, A.L. Baner, Plastic Packaging: Interactions with Food and Pharmaceuticals, Wiley VCH, 2nd Completely Revised Edition, Feb. 13, 2008.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Crowley MM,Drug Dev Ind Pharm. Sep. 2007;33(9):909-26.
D.A. Dean, E.R. Evans, I.H. Hall, Pharmaceutical Packaging Technology, Taylor & Francis, 1st Edition, Nov. 30, 2000.
Dexheimer, Terahertz Spectroscopy: Principles and Applications (Optical Science and Engineering Series), CRC; 1 edition 2007.
Encyclopedia of Pharmaceutical Technology, Third Edition, vol. 1, edited by James Swarbrick. Informa Healthcare, 3rd Edition, Oct. 25, 2006.
Encyclopedia of Pharmaceutical Technology, Third Edition, vol. 2, edited by James Swarbrick. Informa Healthcare, 3rd Edition, Oct. 25, 2006.
Encyclopedia of Pharmaceutical Technology, Third Edition, vol. 3, edited by James Swarbrick. Informa Healthcare, 3rd Edition, Oct. 25, 2006.
Encyclopedia of Pharmaceutical Technology, Third Edition, vol. 4, edited by James Swarbrick. Informa Healthcare, 3rd Edition, Oct. 25, 2006.
Encyclopedia of Pharmaceutical Technology, Third Edition, vol. 5, edited by James Swarbrick. Informa Healthcare, 3rd Edition, Oct. 25, 2006.
Encyclopedia of Pharmaceutical Technology, Third Edition, vol. 6, edited by James Swarbrick. Informa Healthcare, 3rd Edition, Oct. 25, 2006.
Y.-S. Lee et al., Principles of Terahertz Science and Technology (Lecture Notes in Physics), Springer; 1 edition 2008.
R.E. Miles et al., Terahertz Frequency Detection and Identification of Materials and Objects (NATO Science for Peace and Security Series B: Physics and Biophysics), Springer; 1 edition 2007.
Guidance for Industry—Statistical Approaches to Establishing Bioequivalence, FDA, BP, Jan. 2001.
Note for Guidance on the Investigation of Bioavailability and Bioequivalence, EMEA, London, Jul. 26, 2001 (CPMP/EWP/QWP/1401/98.
Herbert A. Lieberman, Pharmaceutical Dosage Forms, Tablets, Second Edition, Revised and Expanded, 1990.
Handbook of Pharmaceutical Excipients, 1986, American Pharmaceutical Assocation, Washington, DC and London (Table of Content Only).
1.2 Klass. Von Extrudern Literature S. 12, pp. 3-7.
2.9 Methoden der pharmazeutischen Technologie 143-144.
El-Egakey, Adel et al, Pharmacerutica Acta Helvetiae, vol. 46, Mar. 19, 1070.

(56) References Cited

OTHER PUBLICATIONS

Apicella A., Biomaterials, vol. 14, No. 2, pp. 83-90, 1993.
Bailey F.E., Journal of Applied Polymer Science, vol. 1, Issue No. 1, pp. 56-62, 1959.
Bauer, Coated Pharmaceutical Dosage Forms, CRC Press, 1998, 1-10.
Braun, et al. Angel Orthodontist, vol. 65 (5) pp. 373-377, 1995.
Crowley M.M., Biomaterials 23, 2002, pp. 4241-4248.
Coppens, Pharmaceutical Technology, 62-70, Jan. 2005.
Caraballo, Journal of Controlled Release, vol. 69, pp. 345-355, 2000.
Dow Technical Data, POLYOX, Feb. 2003.
Dow Excipients Chem. of Poly. Water Soluble-Resin 2004.
Dejong (Pharmaceutisch Weekblad Scientific Edition 1987, p. 24-28.
Davies, et al; European Journal of Pharmaceutics and Biopharmaceutics, 67, 2007, pp. 268-276.
Efentakis M.,Pharmaceutical Development and Technology, 5 (3), pp. 339-346, 2000.
European Pharmacopoeia, pharmaceutical technical procedures, 1997, 135.
El-Sherbiny, European Polymer Journal, vol. 41, pp. 2584-2591, 2005.
Follonier N., Drug Development and Industrial Pharmacy, 20(8), pp. 1323-1339, 1994.
Follonier N., Journal of Controlled Release 36, pp. 243-250, 1995.
Fell, et al, Journal of Pharmaceutical Sciences, vol. 59, No. 5, May 1970, pp. 688-691.
Graham N.B., Poly(Ethylene Glycol) Chemistry: Biotechnical and Biomedical Applications, Chapter 17, 1992.
Griffith, Drug Administration, vol. 19, No. 1, pp. 41-42, 2003.
Hanning C.D., British Journal of Anaesthesia, 61, pp. 221-227, 1988.
Janicki S., Acta Pharm. Technol. 33 (3) 154-155, 1987.
Kim C. J. J Pharm. Sciences 1995, 84(3).
Kim, Chem. Pharm Bull. 1992, 40(10), 2800-2804.
J.W. McGinity—Letter of Jan. 26, 2009.
Dr. Rick Matos, Ph.D—Letter Jan. 6, 2011.
Levina, Journal of Pharmaceutical Sciences, vol. 89, No. 6, pp. 703-723, Jun. 2000.
Levina, Drug Development and Industrial Pharmacy, vol. 28, No. 5, pp. 495-514, 2002.
Lockhart et al, "Packaging of Pharnaceuticals and Health Care Products"; Blackie Academic & Professional; First Edition 1996.
Madorsky S.L., Journal of Polymer Science, vol. 84, No. 3, Mar. 1959.
Mank R., Pharmazie 44, H. 11, pp. 773-776, 1989.
Mank R., Pharmazie 45, H. 8, pp. 592-593 1990.
Mesiha M.S., Drug Development and Industrial Pharmacy, 19(8), pp. 943-959, 1993.
Moroni A., Drug Development and Industrial Pharmacy, 21(12) pp. 1411-1428, 1995.
Maggi et al., Biomaterials, 2002, 23, 1113-1119.
Miller, Nursing, pp. 50-52, Feb. 2000.
Mitchell, Special Resource, vol. 35, No. 5, pp. 535-557, 2000.
Verna, Manthena et al, Am. J. Drug Deliv. 2004: 2 (1): 43-57.
Ohnishi N., Chem. Pharm. Bull, 35(8), pp. 3511-3515, 1987.
Ozeki T., Journal of Controlled Release 58, pp. 87-95, 1999.
Pharm. Research, 1989, 6(9), 6-98.
Pharm. Research, 1991, 8(10), 8-192.
Prapaitrakul W., J. Pharm. Pharmacol. 43, pp. 377-381, 1991.
Pharmazeutische Biologie—Drogen und ihre Inhaltsstoffe—Scharfstoffdrogen, pp. 82-92 (Wagner).
Proeschel, J. Dent. Res., vol. 81, No. 7, pp. 464-468, 2002.
Remington's Pharmaceutical Sciences, pp. 1553-1593, Ch. 89, 1980, 16th Edition.
Radko S., Applied ad Theoretical Electrophoresis 5, pp. 79-88, 1995.
Remington's Pharmaceutical Sciences 17th ed., 1418 (1985).
Rippie E.G., Journal of Pharmaceutical Sciences, Vo. 58, No. 4, pp. 428-431, Apr. 1969.
Schroeder J.,Granulierung hydrophober Wirkstoffe im Planetwalzenextruder 2003, vol. 65, No. 4, 367-372.
Stafford J., überzogene feste Formen, 1991, 347-68.
Schreirs J., Polymer, vol. 32, No. 11, 1991.
Shivanand P.Pharmaceutical Research, Oct. 1991, vol. 8, No. 10.
Sprockel O.L., J. Pharma. Pharmacol. 42, pp. 152-157, 1990.
Stringer J.L., Journal of Controlled Release 42, pp. 195-202, 1996.
Summers et al; Journal of Pharmaceutical Sciences, vol. 66, No. 8, Aug. 1977, pp. 1172-1175.
Third Party Observations, Feb., 2, 2009.
Thoma V.K., Pharm. Ind. 51, Nr. 3, 1989.
Tipler, et al, Physics for Scientists and Engineers, 6th Edition, pp. 234-235, 2003.
US Pharmacopoeia, Chapter 1217, Aug. 1, 2008.
Wikipedia—inert gas data sheet , Dec. 2009.
Yang, Journal of Pharmaceutical Sciences, vol. 85, No. 10, Oct. 1996.
Yarbrough et al, Letters to Nature 322, 347-349 (Jul. 24, 1986) "Extraordinary effects of mortar-and-pestle grinding on microstructure of sintered alumina gel".
Zhang et al., Pharmaceutical Development and Technology, 1999, 4, 241-250.
Jannetto, P. et al, "Oxycodone: Recognition and Pharmacogenomics," Toxicology News, Mar. 2003, 1-7.
Kolter, K., "Compression Behaviour of Kollidon SR," APV/ APGI 2002, Florence, Apr. 11, 2002.
Mises à jour cumulatives, Vidal, Jan./Oct. 2002.
Oxycodon (Oxygesic): Missbrauch, Abhaengigkeit und toedliche Folgen durch Injection zerstossener Retardtabletten, Deutsches Ärzteblatt, vol. 36, A2326-A2326, Sep. 5, 2003.
Oxycontin: Balancing Risks and Benefits, United States Senate, Hearing, Feb. 12, 2002.
Pontier, C. et al, "Use of cycles of compression to characterize the behavior of apatitic phosphate powders," Journal of the European Ceramic Society 22 (2002), 1205-1216.
Silver, J. "Painkiller OxyContin 'most commonly abused prescription drug on the streets of Western Pennsylvania'", Pittsburg Post-Gazette, Apr. 8, 2001.
Wikipedia—Dextromethorphan Aug. 12, 2013 (and attached related English-language entry dated Dec. 11, 2013).
Albertini, B. "New spray congealing atomizer for the microencapsulation of highly concentrated solid and liquid substances," European Journal of Pharmaceutics and Biopharmaceutics 69 (2008) 348-357.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Bennet et al., "A peripheral mononeuropathy in rat that produces disorders of pain sensation like those seen in man", Pain, 33 (1988), pp. 87-107.
Carey et al., Advanced Organic Chemistry, Part A: Structure and Mechanism, Fifth Edition, 2007, Table of Contents, pp. i-xxi.
Carey et al., Advanced Organic Chemistry, Part B: Reactions and Synthese, Fifth Edition, 2007, Table of Contents, pp. i-xxx.
Cheng et al., "Relationship Between the Inhibition Constant (KI) and the Concentration of Inhibitor which Causes 50 Per Cent Inhibition (I50) of an Enzymatic Reaction", Biochemical Pharmacology, vol. 22, 1973, pp. 3099-3108.
Dachille et al., "High-pressure Phase Transofromations in Laboratory Mechanical Mixers and Mortars", Nature, vol. 186, Apr. 2, 1960, pp. 34 and 71.
D'Amour et al., "A Method for Determining Loss of Pain Sensation", Loss of Pain Sensation, 1941, pp. 74-79.
Dubuisson et al., "The Formalin Test: A Quantitative Study of the Analgesic Effects of Morphine, Meperidine, and Brain Stem Stimulation in Rats and Cats", Pain, 4 (1977), pp. 161-174.
Kim et al., "An Experimental Model for Peripheral Neuropathy Produced by Segmental Spinal Nerve Ligation in the Rat", Pain, 50 (1992), pp. 355-363.
Liu et al., "Properties of Lipophilic Matrix Tables Containing Phenylpropanolamine Hydrochloride Prepared by Hot-Melt Extrusion", European Journal of Pharmaceutics and Biopharmaceutics, 52 (2001), pp. 181-190.
Repka et al., Bioadhesive Properties of Hydroxypropylcellulose Topical Films Produced by Hot-Melt Extrusion, Journal of Controlled Release, 70 (2001), pp. 341-351.

(56) References Cited

OTHER PUBLICATIONS

Smith et al., March's Advanced Organic Chemistry, Sixth Edition, 2007, Table of Contents, pp. xiii-xiv.
Smith, Compendium of Organic Synthetic Methods, vol. 12, Wiley, 2009, Table of Contents, pp. i-xviii.
João F. Pinto et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
European Search Report for related EP 12 00 2708.1-1219, mailed Sep. 24, 2012.
European Search Report, Application No./Patent No. 12003743.7-1219, Sep. 24, 2012.
Henrist et al. In vitro and in vivo evaluation of starch-based hot stage extruded double matrix systems. Journal of Controlled Release. 2001, vol. 75, pp. 391-400.
McNeill et al. Properties controlling the diffusion and release of water-soluble solutes from poly(ethylene oxide) hydrogels. 4. Extended constant rate release from partly-coated spheres. Journal Biomat. Sci. Polynn. Ed. 1996, vol. 7, pp. 953-963.
Pillay et al. A novel approach for constant rate delivery of highly soluble bioactives from a simple monolithic system. Journal of Controlled Release. 2000, vol. 67, pp. 67-78.
Evonik Industries, Eudragit Application Guidelines, 10th Edition, 2008, Table of Contents.
PCT International Search Report and Written Opinion for PCT Application No. PCT/EP2014/0777748 dated Feb. 12, 2015.
PCT International Search Report and Written Opinion for PCT Application No. PCT/EP2014/075618 dated Feb. 11, 2015.
Eudragit NE40D web page from Evonik website; downloaded Feb. 24, 2015.
Eudragit RS PO web page from Evonik website; downloaded Feb. 24, 2015.
Glyceryl behenate monograph; European Pharmacopeia 5.0; dated Jan. 2005; downloaded Feb. 24, 2015.
Dierickx et al., "Co-extrusion as manufacturing technique for fixed-dose combination mini-matrices," European Journal of Pharmaceutics and Biopharmaceutics 81 (2012), 683-689.
Eggleston, "The seat of the emetic action of various drugs," J. Pharmacol. Exp. Ther. 7, 225-253 (1915).
European Search Report and Opinion Application No. 14176277.3-1460, Dec. 15, 2014.
European Search Report and Written Opinion for EP Application No. 14169801.9-1455 Oct. 20, 2014.
Evonik Rohm GmbH product brochure: EUDRAGIT acrylic polymers for solid oral dosage forms (2009).
Morissette et al. Advanced Drug Delivery Review 26 (2004), 275-300.
Oliveira et al., "Production and characterization of laminar coextrudates at room temperature in the absence of solvents," AAAPS Annual Meeting and Exposition, Oct. 14-18, 2012, Chicago, USA.
Quintavalle et al., "Preparation of sustained release co-extrudates by hot-melt extrusion and mathematical modelling of in vitro/in vivo drug release profiles," European Journal of Pharmaceutical Sciences 33 (2008), 282-293.
Rosiaux et al. "Ethanol-resistant ethylcellulose/guar gum coatings—Importance for formulation parameters" European Journal of Pharmaceutics and Biopharmaceutics, vol. 85, No. 3, (Jul. 25, 2013). pp. 1250-1258.
Salomies et al., "Determination of Oxycodone Hydrochloride in Oral Solutions by High-Performance Thin-Layer Chromatography/Densitometry," Journal of AOAC International, 83: 1497-1501 (2000).
Vippagunta et al. Advanced Drug Delivery Review 48 (2001), 3-26.
Moorman-Li, R. et al, "A Review of Abuse-Deterrent Opioids for Chronic Nonmalignant Pain." Pharmacy and Therapeutics, vol. 37 No. 7, Jul. 2012, pp. 412-421.
West, Anthony R., Solid state chemistry and its applications, Wiley, New York, 1988, p. 358 and 365.
Bruce et al, Properties of hot-melt extuded tablet formulations for the colonic delivery of 5-aminosalicylic acid, European Journal of Pharmaceutics and Biopharmaceutics, 59 (2005) 85-97.
PCT International Search Report and Written Opinion for PCT Application No. PCT/EP2015/061343 dated Jul. 21, 2015.
PCT International Search Report and Written Opinion for PCT Application No. PCT/EP2015/060377 dated Jul. 23, 2015.
Extended European Search Report and Opinion for Application No. EP 15153679.4-1455, Jun. 30, 2015.

* cited by examiner

PROCESS FOR THE PREPARATION OF A SOLID DOSAGE FORM, IN PARTICULAR A TABLET, FOR PHARMACEUTICAL USE AND PROCESS FOR THE PREPARATION OF A PRECURSOR FOR A SOLID DOSAGE FORM, IN PARTICULAR A TABLET

This application is a Continuation of PCT/EP2009/003290 filed May 8, 2009, which claims priority to European application 08008749.7 filed May 8, 2008.

The present invention pertains to a process of homogenously distributing a liquid, in particular a relatively small amount of a liquid, more in particular a relatively small amount of an oily substance, within a solid material so that a powder product is obtained which is suited to be used in the manufacture of a pharmaceutical composition, in particular a solid dosage form, such as for example a tablet, comprising at least one pharmaceutically active ingredient. The invention further pertains to a process for preparing a solid dosage form, such as a tablet, for pharmaceutical use.

BACKGROUND OF THE INVENTION

Usually, with solid oral dosage forms all excipients have to be homogenously distributed therein. Whereas typically solid excipients, irrespective of their relative amounts, can be homogenously mixed without facing any significant problems, it is rather critical to homogenously distribute liquids, more in particular relatively small amounts of an oil, in a solid mixture. For some solid formulations it might even be desirable to homogenously incorporate therein less than 1%, even less than 0.5 wt-% of an oil, e.g. vitamin E. However, it is not always feasible to melt the entire formulation in order to achieve homogenous mixing.

According to U.S. Pat. No. 4,603,143 a free-flowing vitamin E or vitamin E acetate containing powder is obtained by adding a liquid form of a vitamin E or vitamin E acetate in an amount sufficient to yield a content of about 40 to about 60 wt-% to a silicon-containing adsorbent in the form of substantially discrete non-amorphous agglomerates. At least 50% of said agglomerates have to have a minimum length, width, or both of 300 microns. This process does not require any spray-drying technique. It has been observed that the mixing process as such generates some heat while the liquid vitamin is adsorbed on the surface of the adsorbent powder thereby improving the absorption process.

In GB 1,147,210 problems associated with spray-drying processes in the preparation of dry, finely divided, solid, fat-soluble, vitamin-active products shall be overcome by first preparing a colloidal solution from cold water dispersible, non-gelling colloidal material and water, dispersing therein a water-insoluble, fat-soluble, vitamin-active composition to form a first dispersion, then dispersing said first dispersion in a water immiscible dispersing medium whereby a second dispersion is formed. In the following water is extracted at a temperature in the range from −10 to 0° C. by use of a water extracting agent until said colloidal material solidifies, whereby finely divided, solid particles, containing said water-insoluble, fat-soluble vitamin-active composition dispersed therein is formed. Then, at a temperature in the range from −10 to 0° C. solid particles are separated from said dispersing medium. Finally, substantially all residual moisture is removed from said solid particles. According to GB 1,147,210 with vitamin E as the fat-soluble vitamin-active component a finely divided product is obtained having a particle size distribution such that 91.5 wt-% of a product is in the range from −30 mesh to +120 mesh (US screen sizes).

In EP 229 652 B1 it is disclosed that dry potency stabilized, particulate, free-flowing tocopherol compositions which contain 20 to 60 wt-% of tocopherol in its free tocopherol form and 40 to 80 wt-% of a carrier, based on the total weight of carrier and tocopherol, can be obtained by forming an emulsion or slurry therefrom which in addition has to contain a potency stabilizer in an amount from 2 to 50 wt-% based on the total weight of stabilizer and tocopherol. This emulsion or slurry is subjected to spray-drying. Suitable potency stabilizers are reported to be ascorbic acid, a mixture of ascorbic acid and cysteine and a mixture of citric acid and cysteine. The preferred particle size of the spray-dried product lies in the range from 200 to 500 μm.

According to U.S. Pat. No. 4,892,889 a spray-dried vitamin powder suitable for the preparation of direct-compression vitamin tablets is obtained by spray-drying in a conventional spray-dryer a mixture comprising a fat-soluble vitamin, gelatin having a bloom number between 30 and 300, a water-soluble carbohydrate, and an effective amount of water to permit spray-drying. The final powder shall contain from 20 to 60 wt-% of the fat-soluble vitamin, from 6 to 46 wt-% of the gelatin, and an effective amount of said carbohydrate to prevent extrusion.

In U.S. Pat. No. 4,262,017 a process for the preparation of a vitamin E dry powder having a high content of vitamin E is disclosed which requires dissolving sodium or potassium caseinate in a very specific residual liquor from the production of lactose. The obtained solution has to be mixed with oily vitamin E acetate in a pressure homogenizer to form a dispersion which is subjected to spray-drying to form a powder containing lactose, sodium or potassium caseinate and vitamin E acetate. The final powder product has to contain from 10 to 60 wt-% of vitamin E acetate.

In WO 96/03979 A1 solid dosage forms exhibiting controlled release of an active ingredient can be obtained by spray drying or spray congealing if an atomizing device is employed which uses mechanical vibrations of resonant metal elements or nozzles. According to a preferred embodiment, the resonant metal element comprises an appropriately shaped sonotrode. With the method according to WO 96/03979 A1 the overall dimension of the equipment necessary to obtain solid dosage forms with controlled release can be minimized.

Document WO 98/35655 A2 discloses a process for incorporating at least two incompatible active ingredients into a solid dosage form in such a manner that these ingredients are not in contact with each other. This is accomplished by first distributing the first active ingredient into a lipid or lipoid component having a higher melting point and subsequently mixing the second active ingredient with said granulated higher melting lipid which contains the first active ingredient and with another lipid or lipoid component having a lower melting point. The weight ratio of the higher melting lipid and the lower melting lipid has to be in the range from 1:5 to 5:1. It is described that the first active ingredient can be incorporated into the higher melting lipid or lipoid component by way of spray congealing.

According to WO 99/12864 A2 stearic acid wax, glyceryl fatty acid esters, glyceryl monostearate and lauric acid wax after having been mixed with an active pharmaceutical agent can be subjected to spray congealing. Similarly, in WO 95/17174 A1 it is disclosed to spray congeal a mixture comprising a material selected from the group consisting of $C_{14-18}$ fats, $C_{16-20}$ fatty acids, and $C_{14-18}$ waxes, and dioctylsulfosuccinate.

With the aforementioned established procedures generally only large amounts of vitamin E or derivatives thereof can be employed. It, thus, would have been desirable to be also in the position to homogenously incorporate oily compounds such as vitamin E in rather small amounts into solid excipients used for the manufacture of tablets.

Therefore, it has been an object of the present invention to provide a process for homogenously incorporating a component being in liquid form at ambient temperature or having a waxy consistency, in particular small amounts of such a component, such as for example a waxy or, in particular, oily substance, into a solid component, in particular relatively large amounts of a solid component. The process for homogenously incorporating a liquid into a solid component is preferably also a continuous process enabling the processing of larger amount on an industrial scale. The thus obtained powder with a good, an acceptable blend uniformity (uniform distribution, preferably a relative standard deviation up to 6% (see below in example 5), of the component being in liquid form at ambient temperature or having a waxy consistency in the obtained powder) can then be used for the manufacture of a solid dosage form, in particular a solid dosage form for pharmaceutical use, such as a tablet, capsule, bead, pellet. Further, it has been an object of the present invention to provide a method for manufacturing a solid dosage form, such as for example a tablet, which comprises a component being in liquid form at ambient temperature or having a waxy consistency, in particular relatively small amounts of such a component, e.g. an oily substance, being homogeneously distributed within said solid dosage form. The thus obtained solid dosage form, in particular the tablet, has a good, an acceptable content uniformity for the said component. It has been another object of the present invention to provide a versatile basis for the production of a solid dosage form while keeping various pathways open to arrive at a final solid dosage form thereby furnishing a greater flexibility.

SUMMARY OF THE INVENTION

According to one aspect the problem underlying the present invention has been solved by a process for preparing a powder comprising the steps of
  i) providing at least one first component being in liquid form at ambient temperature, in particular having a viscous liquid consistency, such as for example an oil; or having a waxy consistency at ambient temperature, in particular a component which is a solid or semi-solid at ambient temperature and which has an onset of melting in the temperature range from 15° C. to 40° C.,
  ii) providing at least one second component having a melting point or melting range in the range from above ambient temperature to below the degradation temperature of said first component, in particular in the range from above ambient temperature to 120° C., more in particular in the range from >40° C. to 120° C., even more in particular in the range from 50° C. to 120° C., even further in particular in the range from 55° C. to 120° C.,
  iii) forming a homogenous liquid mixture comprising said at least one first component and said at least one second component by stirring and heating the mixture to or keeping the mixture at a temperature in the range from above the melting point or melting range of said second component and below the degradation temperature of said first component, in particular in the range from above the melting point or melting range of said second component to 120° C.,
  iv) transferring the liquid mixture to at least one spray congealing unit by at least one transfer unit, which is adapted to keep the mixture in its liquid form during its transfer,
  v) spray congealing said mixture, and
  vi) isolating the powder obtained upon spray congealing.

DETAILED DESCRIPTION

A component with a waxy consistency at ambient temperature in the meaning of the present invention can be defined as a component which is a solid or semi-solid at ambient temperature and which has an onset of melting in the temperature range from 15° C. to 40° C.

In the meaning of the present invention the at least one first component being in liquid form at ambient temperature or having a waxy consistency at ambient temperature represents an organic molecule, including oligomers and polymers, i.e. not an inorganic compound. These compounds degrade, that is, loose their original structure when exposed to heat, e.g. by rupture of single or double bonds or by oxidation and/or polymerization reactions. For a specific compound a certain amount of energy/heat is needed to initiate degradation. This is known to a person skilled in the art and is, for example, well reflected in WO 2005/053656 A1.

Further, in the meaning of the present invention the at least one first component is provided in liquid form at ambient temperature or has a waxy consistency at ambient temperature. That is, said first component is employed, e.g. when in the form of an oil, having an inner structure remote from a crystal.

According to one embodiment, the homogenous liquid mixture comprises at least 50 wt % of said at least one second component and 50 wt % or less of said at least one first component; in particular the homogenous liquid mixture comprises at least 75 wt % of said at least one second component and 25 wt % or less of said at least one first component; more in particular the homogenous liquid mixture comprises at least 90 wt % of said at least one second component and 10 wt % or less of said at least one first component; even more in particular the homogenous liquid mixture comprises at least 92 wt % of said at least one second component and 8 wt % or less of said at least one first component; even further in particular the homogeneous liquid mixture comprises at least 94 wt % of said at least one second component and 6 wt % or less of said at least one first component; more in particular the homogeneous liquid mixture comprises at least 96 wt % of said at least one second component and 4 wt % or less of said at least one first component. According to another embodiment, the homogenous liquid mixture comprises from about 92 wt % to about 99.9 wt %, in particular from about 94 wt % to about 99.5 wt %, more in particular from about 94 wt % to about 98 wt % or from about 95 wt % to about 99 wt % or from about 96 wt % to about 99 wt % or from about 95 wt % to about 98 wt % or from about 96 wt % to about 98 wt % of the at least one second component, and from about 0.1 wt % to about 8 wt %, in particular from about 0.5 wt % to about 6 wt %, more in particular from about 2 wt % to about 6 wt % or from about 1 wt % to about 5 wt % or from about 1 wt % to about 4 wt % or from about 2 wt % to about 5 wt % or from about 2 wt % to about 4 wt % of the at least one first component.

According to another embodiment the process for preparing a powder product further comprises keeping the isolated powder at a temperature below the melting point or melting range of said second component, in particular until it is used in the production of a solid dosage form.

Said first component preferably is in liquid form at ambient temperature, in particular has an oily consistency at ambient temperature. Ambient temperature in the meaning of the invention typically comprises temperatures in the range from about 18° C. to about 25° C., and in particular in the range from 20° C. to 25° C. A first component being liquid in the meaning of the present invention also includes compounds or mixtures of compounds which are viscous at ambient temperature allowing, for example, to be transferred through a feed line, if need be, by way of pressure. Suitable oily or waxy first components include, for example, vegetable, animal, mineral and synthetic oils or waxes, e.g. silicon oils or waxes, poloxamers liquid at room temperature, polyethyleneglycols with molecular weight <3000, and mixtures thereof. Mineral oils or waxes for example include paraffin oil or wax, in particular an iso-paraffin oil or wax. Suitable silicon oils comprise dimethicone, substituted and linear dimethicone, simethicone, cyclomethicone and mixtures thereof. Suitable vegetable oils comprise linseed oil, palm oil, olive oil, castor oil, rapeseed oil, soy oil, peanut oil, coconut oil, sunflower oil or turnip seed oil or mixtures thereof. Oils in the meaning of the present invention further comprise alkyl esters of fatty acid esters, wherein the alkyl group has from 1 to 30 carbon atoms and the fatty acid has from 12 to 28 carbon atoms, long chain fatty alcohols or fatty acids (e.g. octyl dodecanol, oleyl alcohol, oleic acid). A particular sub-group are the $C_{1-4}$ alkyl esters of $C_{16-18}$ fatty acids, for example the methyl, ethyl or isopropyl esters of palmitic, heptadecanoic, myristic or stearic acid. Also included are fatty acid glycerides and fatty acid partial glycerides. Suitable waxes in the meaning of the present invention refer to oil-soluble materials which have a waxy consistency and have an onset of melting in the temperature range from 15° C. to 40° C., such as for example lecithine. In a preferred embodiment the first component comprises or represents at least one vitamin oil, lecithine, simethicone or a mixture thereof. In a further preferred embodiment the first component comprises or represents a component selected from vitamin oil, lecithine or simethicone. In a most preferred embodiment the first component comprises or represents a vitamin oil, such as for example tocopherol and/or a tocopherol derivative. Tocopherol comprises alpha-, beta-, gamma-, delta-, and epsilon-tocopherol (determined by the number of methyl groups on the chromanol ring), including its stereoisomeric forms. Various mixtures of the aforementioned tocopherol compounds can also be used. Among the aforementioned components alpha-tocopherol is most preferred. Suitable tocopherol derivatives include tocopherol esters such as dl-tocopheryl acetate. Tocopherol and tocopherol derivatives can be used as active ingredients and/or anti-oxidants with the powders obtained by spray congealing.

Preferably, said first component is a liquid anti-oxidant, e.g. alpha-tocopherol.

Said second component preferably is a component with a melting point or melting range of or above 37° C. but which is not too high, in order to reduce energy input during the spray congealing process. Preferably, the second component does not thermally degrade shortly above its melting point. Exemplary, the melting point or melting range of the second component ranges from above ambient temperature to 120° C., in particular ranges from >40° C. to 120° C., more in particular ranges from 50° C. to 120° C., even more in particular ranges from 55° C. to 120° C. Preferably, the melting point or melting range of the second component should not exceed 90° C., preferably the melting point or melting range of the second component ranges from >40° C. to 90° C., more preferably from 45° C. to 90° C.; even more preferably from 48° C. to 77° C. Preferably, the second component is a component which cools down rapidly. Suitable components to be used as second component comprise hydrophilic polymers such as for example polyalkylene glycol, in particular polyethylene glycol, poly(alkylene oxide), in particular poly(ethylene oxide), poly(vinylalcohol), hydroxymethyl cellulose, hydroxyethyl cellulose, hydroxylpropyl cellulose, hydroxypropyl methylcellulose, carboxy methyl cellulose, and mixtures thereof; waxes or waxy material, such as for example yellow or white wax USP, glyceryl tristearate, carnauba wax, hydrogenated vegetable oil e.g. hydrogenated castor oil, cetyl alcohol, lanolin alcohol, glyceryl monostearate optionally in combination with aminoalkyl methacrylate copolymer E, beeswax, microcrystalline waxes (or microwaxes), gelucire 50/13, polyoxylglycerides, e.g. stearoyl macrogolglycerides, glyceryl behenate, e.g. Compritol 888 ATO®, glyceryl palmitostearate, e.g. Precirol ATO 5®, Vitamin E TPGS (tocopherol glyceryl succinate), and/or mixtures thereof. Preferable components to be used as second component comprise polyalkylene glycol, in particular polyethylene glycol, poly(alkylene oxide), in particular poly(ethylene oxide), waxes or waxy material, such as for example yellow or white wax USP, glyceryl tristearate, carnauba wax, hydrogenated vegetable oil e.g. hydrogenated castor oil, cetyl alcohol, lanolin alcohol, glyceryl monostearate optionally in combination with aminoalkyl methacrylate copolymer E, beeswax, microcrystalline waxes (or microwaxes), gelucire 50/13, polyoxylglycerides, e.g. stearoyl macrogolglycerides, glyceryl behenate, e.g. Compritol 888 ATO®, glyceryl palmitostearate, e.g. Precirol ATO 5®, Vitamin E TPGS (tocopherol glyceryl succinate), and/or mixtures thereof.

The at least one second component preferably comprises at least one polyalkylene glycol, in particular polyethylene glycol, such as polyethylene glycol 3000 to 20000, preferably polyethylene glycol 6000 (PEG 6000). More preferably, the at least one second component consists of polyalkylene glycol, in particular polyethylene glycol, such as polyethylene glycol 3000 to 20000, preferably polyethylene glycol 6000 (PEG 6000).

Preferably, said second component is a component sensitive to oxidation, e.g. polyalkylene glycol, in particular polyethylene glycol, more in particular PEG 6000.

Said homogenous liquid mixture is, according to one embodiment of the present process for preparing a powder, obtained by adding said at least one first component to said at least one second component, which is present in liquid form due to heating.

Said homogenous liquid mixture preferably comprises, or in particular consists of, tocopherol, in particular alpha-tocopherol, as the first component and polyalkylene glycol, in particular polyethylene glycol, more in particular PEG 6000, as the second component.

Spray congealing as such is well known in the art. In the spray congealing process a substance or mixture in its molten state is sprayed into a chamber by use of a so-called atomizing gas to form small droplets. In the spraying chamber, the temperature is below that of the melting point of the sprayed molten substance or mixture so that the small droplets solidify to form a powdered product. With the process of the present invention, it has been found that upon spray congealing a liquid, even very low amounts of the first component, in particular a component being in liquid form, e.g. an oily substance, can be homogeneously distributed within, in particular within the bulk mass of, the second component which is in solid state at ambient temperature. The equipment that can be used for spray congealing is known to a person skilled in the art.

In the spray congealing step usually a heated atomizing gas, preferably an inert gas, e.g. nitrogen, is used with the spray congealing unit having a temperature at the spraying nozzle in the range from about 60° C. to about 120° C., in particular from about 80° C. to about 120° C., in particular from about 95° C. to about 110° C. Preferably, with the spray congealing unit an atomizing gas rate in the range from about 20 kg/h to about 50 kg/h, in particular from about 25 kg/h to about 45 kg/h, is employed. According to a further aspect of the process for preparing a powder, the process gas, e.g. nitrogen gas, used with the spray congealing unit for cooling the sprayed droplets has a temperature in the range from about 0° C. to about 15° C., in particular from about 2° C. to about 12° C. The spray congealing unit preferably comprises at least one spraying nozzle, preferably a two fluid nozzle, said spraying nozzle preferably having a diameter in the range from about 1 mm to about 4 mm, in particular from about 1.5 mm to about 3 mm, more in particular from about 1.5 mm to about 2 mm. It is considered to be within the skills of the skilled person to recognize the most appropriate parameters of the spray congealing process taking into account the type of apparatus used, the desired viscosity of the homogeneous mixture, the thermostability of the mixture, the size of the batch and the like.

In one embodiment of the process, said transfer unit comprises at least one, in particular one, feed line and at least one, in particular one, pump, wherein at least said feed line is adapted to be heatable. Said at least one second component preferably is at least partially melted in the transfer unit, in particular in the feed line. In this embodiment, the at least one first component is preferably added to the molten second component prior to entering the spray nozzle, e.g. the at least one first component is added to the molten second component in the feed vessel or the feed line. Preferably, the feed vessel is adapted to be heatable. Preferably, both the feed vessel and the feed line is heated.

Accordingly, the powder obtained with the present invention preferably comprises, more particularly consists of, at least 75 wt % of polyalkylene glycol, in particular polyethylene glycol, more in particular PEG 6000, and 25 wt % or less of tocopherol, in particular alpha-tocopherol; more in particular the powder comprises, more particularly consists of, at least 90 wt % of polyalkylene glycol, in particular polyethylene glycol, more in particular PEG 6000, and 10 wt % or less of tocopherol, in particular alpha-tocopherol; even more in particular the powder comprises, more particularly consists of, at least 92 wt % of polyalkylene glycol, in particular polyethylene glycol, more in particular PEG 6000, and 8 wt % or less of tocopherol, in particular alpha-tocopherol. According to another embodiment, the powder obtained with the present invention preferably comprises, more particularly consists of, from about 92 wt % to about 99.9 wt %, in particular from about 94 wt % to about 99.5 wt %, more in particular from about 96 wt % to about 99 wt %, even more in particular from about 96 wt % to about 98 wt % of polyalkylene glycol, in particular polyethylene glycol, more in particular PEG 6000, and from about 0.1 wt % to about 8 wt %, in particular from about 0.5 wt % to about 6 wt %, more in particular from about 1 wt % to about 4 wt %, even more in particular from about 2 wt % to about 4 wt % of tocopherol, in particular alpha-tocopherol. According to yet another embodiment, the powder obtained with the present invention preferably comprises, more particularly consists of, from about 92 wt % to about 99.9 wt %, in particular from about 94 wt % to about 99.5 wt %, more in particular from about 94 wt % to about 98 wt % or from about 95 wt % to about 99 wt % or from about 96 wt % to about 99 wt % or from about 95 wt % to about 98 wt % or from about 96 wt % to about 98 wt % of the at least one second component, and from about 0.1 wt % to about 8 wt %, in particular from about 0.5 wt % to about 6 wt %, more in particular from about 2 wt % to about 6 wt % or from about 1 wt % to about 5 wt % or from about 1 wt % to about 4 wt % or from about 2 wt % to about 5 wt % or from about 2 wt % to about 4 wt % of the at least one first component.

In another embodiment, the powder product obtained with the process of the invention preferably has a particle size distribution (PSD) $d_{50}$ in the range from about 40 μm to about 300 μm, in particular from about 40 μm to about 200 μm, more in particular in the range from about 50 μm to about 180 μm. In case the product particles obtained with the process of the present invention are not essentially spherical in shape, the particle size of such irregularly shaped particles is determined by taking the diameter of a sphere which has essentially the same volume as said irregularly shaped particle. The particle size can, for example, be determined by laser diffraction techniques. The average particle size $d_{50}$ is regularly defined as the size or diameter where 50 mass-% of the particles of the powder have larger diameter and where the other 50 mass-% have a smaller diameter.

A powder obtainable by or obtained with the process of the invention is particularly suited for the preparation of a pharmaceutical solid dosage form, such as for example a capsule or tablet, containing at least one pharmaceutically active ingredient. Therefore, the present invention also relates to the use of a powder obtainable by or obtained with the process of the invention for the preparation of a solid dosage form containing at least one pharmaceutically active ingredient.

With the powder obtained according to the process of the present invention a solid dosage form for pharmaceutical use can be prepared containing less than 1 wt %, in particular less than 0.4 wt %, e.g. in the range from about 0.05 to about 0.3 wt % or in the range from about 0.1 to about 0.15 wt %, of said first component based on the total weight of the solid dosage form. Preferably, the first component is homogeneously/uniformly distributed in said solid dosage form.

According to another aspect the problem underlying the present invention has been solved by a process for the preparation of a solid dosage form, in particular a tablet, comprising the steps of a) providing at least one pharmaceutically active ingredient (component a),
b) providing the powder according to the above spray congealing process according to the invention (component b),
c) providing at least one third component (component c),
d) forming a mixture comprising components a, and b and c),
e) transforming said mixture into a solid dosage form.

It is evident that in case the pharmaceutically active ingredient is a component being in liquid form at ambient temperature or having a waxy consistency at ambient temperature, that the pharmaceutically active ingredient can be incorporated in the powder according to the spray congealing process of the present invention and hence, the present invention also comprises a process for the preparation of a solid dosage form comprising the steps of a) providing the powder according to the above spray congealing process according to the invention, wherein the first component, in particular the first liquid component, is a pharmaceutically active ingredient and wherein the at least one second component is as defined above, (component a),
b) providing at least one third component (component b),
c) forming a mixture comprising components a) and b),
d) transforming said mixture into a solid dosage form.

The mixture under c) can for instance be formed by blending e.g. in a fluid bed or by wet-, dry- or melt-granulation in a high or low shear granulator, or by slugging (roller compactor).

Suitable pharmaceutically active ingredients are those which exert a local physiological effect, as well as those which exert a systemic effect, after oral administration. Examples of suitable active ingredients encompass:

analgesic and anti-inflammatory drugs (NSAIDs, fentanyl, indomethacin, ibuprofen, ketoprofen, nabumetone, paracetamol, piroxicam, tramadol, tapentadol, COX-2 inhibitors such as celecoxib and rofecoxib);

anti-arrhythmic drugs (procainamide, quinidine, verapamil); antibacterial and antiprotozoal agents (amoxicillin, ampicillin, benzathine penicillin, benzylpenicillin, cefaclor, cefadroxil, cefprozil, cefuroxime axetil, cephalexin, chloramphenicol, chloroquine, ciprofloxacin, clarithromycin, clavulanic acid, clindamycin, doxyxycline, erythromycin, flucloxacillin sodium, halofantrine, isoniazid, kanamycin sulphate, lincomycin, mefloquine, minocycline, nafcillin sodium, nalidixic acid, neomycin, norfloxacin, ofloxacin, oxacillin, phenoxymethyl-penicillin potassium, pyrimethamine-sulfadoxime, streptomycin);

anti-coagulants (warfarin);

antidepressants (amitriptyline, amoxapine, butriptyline, clomipramine, desipramine, dothiepin, doxepin, fluoxetine, reboxetine, amineptine, selegiline, gepirone, imipramine, lithium carbonate, mianserin, milnacipran, nortriptyline, paroxetine, sertraline; 3-[2-[3,4-dihydrobenzofuro[3,2-c]pyridin-2(1H)-yl]ethyl]-2-methyl-4H-pyrido[1,2-a]pyrimidin-4-one);

anti-diabetic drugs (glibenclamide, metformin);

anti-epileptic drugs (carbamazepine, clonazepam, ethosuximide, gabapentin, lamotrigine, levetiracetam, phenobarbitone, phenyloin, primidone, tiagabine, topiramate, valpromide, vigabatrin); antifungal agents (amphotericin, clotrimazole, econazole, fluconazole, flucytosine, griseofulvin, itraconazole, ketoconazole, miconazole nitrate, nystatin, terbinafine, voriconazole);

antihistamines (astemizole, cinnarizine, cyproheptadine, decarboethoxyloratadine, fexofenadine, flunarizine, levocabastine, loratadine, norastemizole, oxatomide, promethazine, terfenadine); anti-hypertensive drugs (captopril, enalapril, ketanserin, lisinopril, minoxidil, prazosin, ramipril, reserpine, terazosin);

anti-muscarinic agents (atropine sulphate, hyoscine);

antineoplastic agents and antimetabolites (platinum compounds, such as cisplatin, carboplatin; taxanes, such as paclitaxel, docetaxel; tecans, such as camptothecin, irinotecan, topotecan; vinca alkaloids, such as vinblastine, vindecine, vincristine, vinorelbine; nucleoside derivatives and folic acid antagonists such as 5-fluorouracil, capecitabine, gemcitabine, mercaptopurine, thioguanine, cladribine, methotrexate; alkylating agents, such as the nitrogen mustards, e.g. cyclophosphamide, chlorambucil, chlormethine, iphosphamide, melphalan, or the nitrosoureas, e.g. carmustine, lomustine, or other alkylating agents, e.g. busulphan, dacarbazine, procarbazine, thiotepa; antibiotics, such as daunorubicin, doxorubicin, idarubicin, epirubicin, bleomycin, dactinomycin, mitomycin; HER 2 antibody, such as trastuzumab; podophyllotoxin derivatives, such as etoposide, teniposide; farnesyl transferase inhibitors; anthrachinon derivatives, such as mitoxantron; hdm2 antagonists; HDAC inhibitors; cMet inhibitors);

anti-migraine drugs (alniditan, naratriptan, sumatriptan); anti-Parkinsonian drugs (bromocryptine mesylate, levodopa, selegiline);

antipsychotic, hypnotic and sedating agents (alprazolam, buspirone, chlordiazepoxide, chlorpromazine, clozapine, diazepam, flupenthixol, fluphenazine, flurazepam, 9-hydroxyrisperidone, lorazepam, mazapertine, olanzapine, oxazepam, pimozide, pipamperone, piracetam, promazine, risperidone, selfotel, seroquel, sertindole, sulpiride, temazepam, thiothixene, triazolam, trifluperidol, ziprasidone, zolpidem);

anti-stroke agents (lubeluzole, lubeluzole oxide, riluzole, aptiganel, eliprodil, remacemide); antitussive (dextromethorphan, laevodropropizine);

antivirals (acyclovir, ganciclovir, loviride, tivirapine, zidovudine, lamivudine, zidovudine+lamivudine, didanosine, zalcitabine, stavudine, abacavir, lopinavir, amprenavir, nevirapine, efavirenz, delavirdine, indinavir, nelfinavir, ritonavir, saquinavir, adefovir, hydroxyurea, etravirine, darunavir, rilpivirine);

beta-adrenoceptor blocking agents (atenolol, carvedilol, metoprolol, nebivolol, propanolol); cardiac inotropic agents (amrinone, digitoxin, digoxin, milrinone);

corticosteroids (beclomethasone dipropionate, betamethasone, budesonide, dexamethasone, hydrocortisone, methylprednisolone, prednisolone, prednisone, triamcinolone);

disinfectants (chlorhexidine);

diuretics (acetazolamide, frusemide, hydrochlorothiazide, isosorbide); enzymes;

essential oils (anethole, anise oil, caraway, cardamom, cassia oil, cineole, cinnamon oil, clove oil, coriander oil, dementholised mint oil, dill oil, eucalyptus oil, eugenol, ginger, lemon oil, mustard oil, neroli oil, nutmeg oil, orange oil, peppermint, sage, spearmint, terpineol, thyme); gastro-intestinal agents (cimetidine, cisapride, clebopride, diphenoxylate, domperidone, famotidine, lansoprazole, loperamide, loperamide oxide, mesalazine, metoclopramide, mosapride, nizatidine, norcisapride, olsalazine, omeprazole, pantoprazole, perprazole, prucalopride, rabeprazole, ranitidine, ridogrel, sulphasalazine);

haemostatics (aminocaproic acid);

lipid regulating agents (atorvastatin, lovastatin, pravastatin, probucol, simvastatin); local anaesthetics (benzocaine, lignocaine);

opioid analgesics (buprenorphine, codeine, dextromoramide, dihydrocodeine, hydrocodone, oxycodone, morphine);

parasympathomimetics and anti-dementia drugs (ATT-082, eptastigmine, galanthamine, metrifonate, milameline, neostigmine, physostigmine, tacrine, donepezil, rivastigmine, sabcomeline, talsaclidine, xanomeline, memantine, lazabemide); peptides and proteins (antibodies, becaplermin, cyclosporine, erythropoietin, immunoglobulins, insuline);

sex hormones (oestrogens: conjugated oestrogens, ethinyloestradiol, mestranol, oestradiol, oestriol, oestrone; progestogens; chlormadinone acetate, cyproterone acetate, 17-deacetyl norgestimate, desogestrel, dienogest, dydrogesterone, ethynodiol diacetate, gestodene, 3-keto desogestrel, levonorgestrel, lynestrenol, medroxy-progesterone acetate, megestrol, norethindrone, norethindrone acetate, norethisterone, norethisterone acetate, norethynodrel, norgestimate, norgestrel, norgestrienone, progesterone, quingestanol acetate);

stimulating agents (sildenafil);

vasodilators (amlodipine, buflomedil, amyl nitrite, diltiazem, dipyridamole, glyceryl trinitrate, isosorbide dinitrate, lidoflazine, molsidomine, nicardipine, nifedipine, oxpentifylline, pentaerythritol tetranitrate); their N-oxides, their pharmaceutically acceptable acid or base addition salts, their solvates and their stereochemically isomeric forms.

Pharmaceutically acceptable acid addition salts comprise the acid addition salt forms which can conveniently be obtained by treating the base form of the active ingredient with appropriate organic and anorganic acids. Suitable acids are for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfonic, 2-hydroxybenzoic, 4-amino-2-hydroxybenzoic and the like acids. Conversely the salt form can be converted by treatment with alkali into the free base form.

Active ingredients containing an acidic proton may be converted into their non-toxic metal or amine addition salt forms by treatment with appropriate organic and inorganic bases. Appropriate base addition salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like.

The term solvate comprises the hydrates and solvent addition forms which the active ingredients are able to form, as well as the salts thereof. Examples of such forms are e.g. hydrates, alcoholates and the like.

The N-oxide forms of the active ingredients comprise those active ingredients wherein one or several tertiary nitrogen atoms are oxidized to the so-called N-oxide.

The term "stereochemically isomeric forms" defines all the possible stereoisomeric forms which the active ingredients may possess. More in particular, stereogenic centers may have the R- or S-configuration or cis or trans configuration, and active ingredients containing one or more double bonds may have the E- or Z-configuration.

Preferably, the pharmaceutically active ingredient is an analgesic compound, in particular an opioid or opioid derivative, such as for example tapentadol or a pharmaceutically acceptable acid addition salt thereof, such as for example tapentadol HCl.

Suitable first and second components for obtaining the powder according to the present spray congealing process according to the invention as defined in the process for the preparation of a solid dosage form are as defined hereinabove for the spray congealed powder.

Said at least one third component may comprise a hydrophilic polymer, preferably selected from the group consisting of in particular poly(ethylene oxide), poly(vinyl alcohol), hydroxymethyl cellulose, hydroxyethyl cellulose, hydroxypropyl cellulose, hydroxypropyl methylcellulose and carboxy methylcellulose. In a preferred embodiment said hydrophilic polymer comprises poly(alkylene oxide), in particular poly(ethylene oxide) and/or a cellulose derivative, in particular hydroxypropyl methylcellulose. In another preferred embodiment said hydrophilic polymer comprises and in particular essentially consists of poly(alkylene oxide), in particular poly(ethylene oxide), and a cellulose derivative, in particular hydroxypropyl methylcellulose.

Preferably, said at least one third component is a component sensitive to oxidation, e.g. poly(alkylene oxide).

Said at least one third component may also comprise one or more hydrophilic polymers constituting a controlled release matrix preferably releasing the pharmaceutically active ingredient gradually, slowly or continuously. Said polymers swell upon contact with aqueous fluid following administration, regularly resulting in a viscous, drug release regulating gellayer. The viscosity of the polymers preferably ranges from 150 to 100,000 mPa·s (apparent viscosity of a 2% aqueous solution at 20° C.). Examples of such polymers are alkylcelluloses, such as, methylcellulose;
hydroxyalkylcelluloses, for example, hydroxymethylcellulose, hydroxyethylcellulose, hydroxypropylcellulose and hydroxybutylcellulose;
hydroxyalkyl alkylcelluloses, such as, hydroxyethyl methylcellulose and hydroxypropyl methylcellulose;
carboxyalkylcelluloses, such as, carboxymethylcellulose;
alkali metal salts of carboxyalkylcelluloses, such as, sodium carboxymethylcellulose;
carboxyalkylalkylcelluloses, such as, carboxymethylethylcellulose;
carboxyalkylcellulose esters;
other natural, semi-synthetic, or synthetic polysaccharides, such as, alginic acid, alkali metal and ammonium salts thereof, carrageenans, galactomannans, tragacanth, agar-agar, gummi arabicum, guar gummi, xanthan gummi, starches, pectins, such as sodium carboxymethylamylopectin, chitin derivates such as chitosan, polyfructans, inulin;
polyacrylic acids and the salts thereof;
polymethacrylic acids and the salts thereof, methacrylate copolymers;
polyvinylalcohol;
polyvinylpyrrolidone, copolymers of polyvinylpyrrolidone with vinyl acetate;
combinations of polyvinylalcohol and polyvinylpyrrolidone;
polyalkylene oxides such as polyethylene oxide and polypropylene oxide and copolymers of ethylene oxide and propylene oxide.

Preferable hydrophilic polymers are polysaccharides, more in particular cellulose derivatives and most in particular cellulose ether derivatives.

Most preferred cellulose ether derivatives are hydroxypropyl methylcellulose and hydroxypropyl cellulose, in particular hydroxypropyl methylcellulose.

Different viscosity grades of hydroxypropyl cellulose and hydroxypropyl methylcellulose are commercially available.

Hydroxypropyl methylcellulose preferably has a viscosity grade ranging from about 3,500 mPa·s to about 100,000 mPa·s, in particular ranging from about 4,000 mPa·s to about 20,000 mPa·s and most in particular a viscosity grade of about 6,500 mPa·s to about 15,000 mPa·s (apparent viscosity of a 2% aqueous solution at 20° C.). Exemplary hydroxypropyl methylcellulose are e.g. hypromellose 2208 (DOW, Antwerp, Belgium) or hypromellose 2910. It is considered to be in the knowledge of the skilled person to recognise the appropriate viscosity or substitution grade of hydroxypropyl methylcellulose.

Hydroxypropyl cellulose having a viscosity lower than 1,500 mPa·s (apparent viscosity of a 2% aqueous solution at 20° C.) is preferred, in particular hydroxypropyl cellulose having a viscosity in the range from about 150 to about 700 mPa·s, preferably from 200 to 600 mPa·s, e.g. Klucel EF® (Hercules, Wilminton, USA).

The hydrophilic polymers constituting the matrix mainly provide for the controlled, in particular gradual, slow or continuous, pharmacokinetic release profile of the preparation. Depending on the amount of polymers processed in the preparation, the release profile can be tuned. Preferably, the amount of hydrophilic polymer in the present formulation ranges from about 0.01 to about 80% (w/w), in particular from about 10% to about 80% (w/w), or from about 20% to about 80% (w/w), or from about 30% to about 80% (w/w) or from about 40% to about 80% (w/w). In addition, when using a combination of polymers, the ratio of said polymers also influences the release profile of the preparation. For example, when using one or more hydrophilic polymers, preferably cellulose derivatives, more in particular hydroxypropyl cellulose and hydroxypropyl methylcellulose, the weight percentage (% w/w) of hydroxypropyl methylcellulose preferably ranges from 0 to about 16%; the weight percentage of hydroxypropyl cellulose preferably ranges between about 25% and about 62%. The ratio of hydroxypropyl cellulose to hydroxypropyl methylcellulose preferably ranges from 1:5 to 5:1, more preferable from 1:1 to 5:1, and most preferred from 3:1 to 5:1.

A combination of different polymers offers the possibility of combining different mechanisms by which the active ingredient is released from the matrix. Such combination facilitates control of the pharmacokinetic release profile of the preparation at will. Three main mechanisms exist by which an active ingredient can be released from a hydrophilic matrix: dissolution, erosion and diffusion. An active ingredient will be released by the dissolution mechanism when it is homogeneously dispersed in a matrix network of a soluble polymer. The network will gradually dissolve in the gastro-intestinal tract, thereby gradually releasing its load. The matrix polymer can also gradually be eroded from the matrix surface, likewise releasing the active ingredient in time. When an active ingredient is processed in a matrix made up of an insoluble polymer, it will be released by diffusion: the gastro-intestinal fluids penetrate the insoluble, sponge-like matrix and diffuse back out loaded with drug.

Release of one or more active ingredients from a matrix containing hydroxypropyl cellulose and hydroxypropyl methylcellulose occurs by a combined set of release mechanisms. Due to the higher solubility of hydroxypropyl methylcellulose compared with hydroxypropyl cellulose, the former will gradually dissolve and erode from the matrix, whereas the latter will more act as a sponge-like matrix former releasing the active ingredient mainly by diffusion.

Said at least one third component may also comprise pharmaceutically acceptable formulating agents in order to promote the manufacture, compressibility, appearance and taste of the preparation. These formulating agents comprise, for example, diluents or fillers, glidants, binding agents, granulating agents, anti-caking agents, lubricants, flavors, sweeteners, dyes, pigments and preservatives.

The filler may be selected from soluble fillers, for example, sucrose, lactose, trehalose, maltose, mannitol, sorbitol, inulin, and from insoluble fillers, for example, dicalcium or tricalcium phosphate, dicalcium carbonate, talc, microcrystalline cellulose, silicified microcrystalline cellulose. An interesting filler is lactose, in particular, lactose monohydrate. Different grades of lactose can be used. One type of lactose preferably used in the present invention is lactose monohydrate, in particular 200 mesh (e.g. available from DMV, Veghel, the Netherlands). Another preferred lactose monohydrate type is characterised in that 98% (w/w) of the particles have a diameter smaller than 250 μm, 30% (w/w) to 60% (w/w) of the particles have a diameter of 100 μm and at maximum 15% (w/w) of the particles have a diameter of smaller than 45 μm. Such lactose monohydrate can for example be purchased as lactose monohydrate of the type DCL 11 from DMV, Veghel, the Netherlands. The notation DCL refers to "Direct Compression Lactose". The number 11 is a reference number of the manufacturer. Another interesting filler is mannitol, such as for instance fine grade mannitol or direct compression mannitol (Roquette).

The weight percentage of filler preferably ranges between 0% to about 54% (w/w), in particular between about 6% and about 54% (w/w).

Among the formulating agents that further may be comprised in the solid dosage form there may be mentioned agents such as polyvidone; starch; acacia gum; gelatin; seaweed derivatives, e.g. alginic acid, sodium and calcium alginate; cellulose derivatives, e.g. ethylcellulose, hydroxypropylmethylcellulose, having useful binding and granulating properties; glidants such as colloidal silica, starch or talc; lubricants such as magnesium stearate and/or palmitate, calcium stearate, stearic acid, polyethylene glycol, liquid paraffin, sodium or magnesium lauryl sulphate; antiadherents such as talc and corn starch.

In addition to the pharmaceutical acceptable formulating agents described above, cyclodextrins or derivatives thereof may also be included to improve the dissolution rate of the active ingredient. The cyclodextrins which can be used includes the pharmaceutically acceptable unsubstituted and substituted cyclodextrins known in the art, more particularly α, β or γ cyclodextrins or the pharmaceutically acceptable derivatives thereof, such as for example β-cyclodextrin ethers, e.g. dimethyl-β-cyclodextrin and polyethers, e.g. hydroxypropyl β-cyclodextrin and hydroxyethyl β-cyclodextrin, being examples. Another suitable type of substituted cyclodextrins is sulfobutylcyclodextrins. This type is also envisaged in the present invention.

Suitable sweeteners include sucrose, glucose, fructose or intense sweeteners, i.e. agents with a high sweetening power when compared to sucrose (e.g. at least 10 times sweeter than sucrose). Suitable intense sweeteners comprise aspartame, saccharin, sodium or potassium or calcium saccharin, acesulfame potassium, sucralose, alitame, xylitol, cyclamate, neomate, neohesperidine dihydrochalcone or mixtures thereof, thaumatin, palatinit, stevioside, rebaudioside, Magnasweet®.

Suitable flavours include fruit flavours such as tutti frutti, cherry, raspberry, black currant or strawberry flavour, or stronger flavours, such as Caramel Chocolate flavour, caramel sweet tone, Mint Cool flavour, Fantasy flavour, vanilla, grenadine, guarana, masking flavour (Givaudan, in particular masking flavour 11031-31) and the like. Combinations of flavours may also be used.

Suitable dyes or pigments include iron oxides or aluminium lakes.

The solid dosage form which can be obtained by the above-described process comprises a tablet, a tablet precursor, a capsule, pellets, beads, and an extrudate.

Transforming the mixture of the components into a solid dosage form as indicated under point e) respectively d) of the above-described processes can be done by using pharmaceutically acceptable processes known to the person skilled in the art, such as for example granulation, tabletting including direct compression, slugging, capsule filling, extrusion, pelletization and the like.

One embodiment of the present invention therefore relates to a process for the preparation of a solid dosage form, in particular a tablet, comprising the steps of a) providing the powder according to the above spray congealing process of the present invention (component a),
b) providing at least one first, in particular solid, pharmaceutically active ingredient (component b) and/or providing at least one second pharmaceutically active ingredient, in particular in the form of the first component, with said powder of step a),
c) providing at least one third component (component c),
d) forming a mixture therefrom,
e) meltextruding said mixture,
f) collecting the extruded product, and
g) compressing the extruded product into a solid dosage form, in particular a tablet.

Preferably, in one embodiment said first pharmaceutically active ingredient, said powder and said third component are solid at ambient temperature.

Upon melt extrusion the extruded product usually is present in the form of at least one strand representing one possible form of the tablet precursor. Alternatively, it is also possible to cut the extruded product, in particular the strand, into individual pieces which represent another form of tablet precursor in the meaning of the present invention. These individual pieces preferably have or approximate the length dimension of the tablet which can be shaped therefrom. It is found to be advantageous for certain embodiments that the strand is cooled below 45° C., below ambient temperature, particularly to temperatures below 10° C. prior to cutting.

The process for preparing a solid dosage form in the meaning of the invention preferably requires that at least components a), b) and c) respectively a) and c) are homogenously mixed prior to transforming the mixture into a solid dosage form, in particular prior to melt extrusion, preferably while at least components a) and b) and said third component c), respectively a) and said third component are in their solid states.

With the process for the preparation of a solid dosage form, preferably an extrudate, preferably at least 5 wt % of said pharmaceutically active ingredient, at least 20 wt % of said at least one third component, in particular comprising, more in particular consisting of, poly(ethylene oxide) and hydroxypropyl methylcellulose, and at least 3 wt % of the spray congealed powder, in particular comprising, more in particular consisting of, a vitamin oil and polyalkylene glycol, in particular tocopherol and PEG 6000 are used. Those powders are particularly preferred as spray congealed powders which comprise 50 wt % or less, in particular 25 wt % or less, more in particular 10 wt % or less, even more in particular 8 wt % or less, even further in particular 6 wt % or less or 4 wt % or less, of said first component, based on the total weight of the spray congealed powder.

According to another aspect of the object of the present invention, there is taught a process for the preparation of a tablet for pharmaceutical application as an oral dosage form comprising the steps of providing at least one tablet precursor obtained according to a process of the present invention, in particular obtained according to the melt extrusion process of the present invention as described hereinabove, subjecting said tablet precursor to a tablet punch, and collecting the tablet or tablets from the tablet punch after the punching step/compression step. According to one mode of executing said process, the tablet precursor is cut from the extrudate in the form of an individual piece, in particular approximating the dimensions of the final tablet, said piece is transferred to the tablet press and subjected to the punching step/compression step, whereupon the punched tablet is collected from the tablet punch. Alternatively, the tablet precursor in the form of an extruded strand is transferred to the tablet press and is as such subjected to the punching step/compression step, whereupon the punched tablets are collected from the tablet punch. In another embodiment, the process for the preparation of the tablet includes that the extruded tablet precursor in the form of a cut individual piece or the tablet precursor in the form of a strand is subjected to the punching step/compression step when still being warm from the melt extrusion process. Alternatively, this process includes that the tablet precursor in the form of a cut individual piece or the tablet precursor in the form of a strand is subjected to the punching step/compression step while having a temperature above ambient temperature and below the melting point or melting range of said at least one second and said at least one third component in said tablet precursor. It is of course also possible that the tablet precursor in the form of a cut individual piece or the tablet precursor in the form of a strand is subjected to the punching step/compression step while having a temperature below ambient temperature, in particular below 15° C.

From the above it can be derived that according to one embodiment, the present invention also relates to a process for producing a tablet comprising the steps of
a) providing a powder according to a process comprising the steps of providing at least one first component being in liquid form at ambient temperature, in particular having a viscous liquid consistency, such as for example an oil; or having a waxy consistency at ambient temperature, in particular a component which is a solid or semi-solid at ambient temperature and which has an onset of melting in the temperature range from 15° C. to 40° C., providing at least one second component having a melting point or melting range in the range from above ambient temperature to below the degradation temperature of said first component, in particular in the range from above ambient temperature to 120° C., more in particular in the range from >40° C. to 120° C., even more in particular in the range from 50° C. to 120° C., even further in particular in the range from 55° C. to 120° C. or not above 90° C., forming a homogenous liquid mixture comprising said at least one first component and said at least one second component by stirring and heating the mixture to or keeping the mixture at a temperature in the range from above the melting point or melting range of said second component and below the degradation temperature of said first component, in particular in the range from above the melting point or melting range of said second component to 120° C., more preferably not above 90° C., transferring the liquid mixture to at least one spray congealing unit by at least one transfer unit, which is adapted to keep the mixture in its liquid form during its transfer, spray congealing said mixture, and isolating the powder obtained upon spray congealing (component a),
b) providing at least one pharmaceutically active ingredient (component b),
c) providing at least one third component (component c),
d) forming a mixture comprising components a, and b and c,
e) meltextruding said mixture,
f) collecting the extruded product, in particular in the form of at least one strand or in the form of individual pieces obtained by cutting said at least one strand;
g) subjecting said extruded product, in particular in the form of at least one strand or in the form of individual pieces obtained by cutting said at least one strand, to a tablet press; and
h) collecting the tablet or tablets from the tablet press after the punching step/compression step.

In a preferred embodiment, the at least one first component is one component, in particular alpha tocopherol, and the at least one second component is one component, in particular polyalkylene glycolpolyalkylene glycol, more in particular poly(ethylene)glycol, even more in particular PEG 6000.

The present invention also relates to a solid dosage form, in particular a tablet, obtainable by or obtained with the process as described hereinabove. Said solid dosage form can also be a tablet precursor such as the product resulting from the above described melt extrusion process, said tablet precursor can be further compressed into a tablet.

With the present invention it has surprisingly been found that even very low amounts of a liquid or waxy compound such as e.g. an oil, can be homogeneously distributed in a material which is solid at ambient temperature in order to form a powder product, preferably having a small particle size distribution and being suited to be used for the preparation of a solid dosage form, in particular a pharmaceutical tablet. With the process of the present invention, it is now advantageously possible to incorporate even tiny amounts of excipients not being solid at ambient temperature, but being liquid or waxy, into a solid dosage form, e.g. a tablet in a homogenous manner. Furthermore, it is possible to finely adjust these very small amounts of products being liquid or waxy at ambient temperature in the final formulations. For example, it is possible to finely adjust the amount of vitamin E/tocopherol in a tablet formulation in the range of from about 0.05 to about 0.5 wt-% based on the weight of the tablet, the property profile of said tablet can be optimized, for example, in terms of storage stability and ease of formulation. The advantageous storage stability feature not only is an advantage for the tablet itself but also for the tablet precursor being used in the tablet punching step/compression step. That is, there is no need to immediately subject the extruded tablet precursor to the tablet punching step/compression step, thereby greatly enlarging the mode of operation for the tablet manufacturer. It is, for example, even possible to ship the tablet precursor of the present invention from one production facility to another production site without affecting the efficacy of the final pharmaceutical tablet formulation. It is another benefit of the present invention that the powder products obtained by the spray congealing process of the present invention regularly do not tend to be sticky at ambient temperature.

The features disclosed in the description as well as in the claims can be used essential alone or in every combination for the realization of the invention in different embodiments. The different embodiments described for the spray congealing process also apply for the process for the preparation of a solid dosage form. As used herein, the term "about" means±10% of the value.

EXAMPLES

Example 1

Preparation of Spray Congealed Powder Having the Following Composition

| | |
|---|---|
| DL-alpha-tocopherol (Vitamin E) | 4.00 wt-% |
| Polyethylene Glycol 6000 (PEG 6000) | 96.00 wt-% |

Melt Preparation Process:

The required amounts of Vitamin E and PEG 6000 were weighed out. An appropriately sized stainless steel feed tank with mixer fitted with a Chromalox Micro Therm temperature control system was purged with nitrogen. PEG 6000 was slowly added into the feed tank. Once partially melted, it was agitated with a mixer to promote melting. Once PEG 6000 was completely added and melted, a melt temperature of 80° C. was maintained. The tank was continuously purged with nitrogen. Vitamin E was added into the molten PEG 6000. It was continued to mix for at least 10 minutes before spray congealing started. Agitation was kept throughout the spray congealing process.

Spray Congealing Process:

The thermal controllers for the feed lines were set at 90° C. and pre-heated for at least 30 minutes.

The spray congealing process was started:
Apparatus: Niro-PSD-2® (two-fluid nozzle with orifice diameter of 2.0 mm)
Atomization gas: nitrogen (80° C.)
Atomization gas pressure 1.0 bar
Process gas: nitrogen, flow rate 425 CMH
Feed rate: 9 kg/h
Outlet temperature: 10° C.
Condenser temperature: 0° C.
Collection of Spray Congealed Powder Spray congealed powder was collected from the cyclone in product drums (purged with nitrogen for a minimum of 5 minutes before sealing).

Example 2

Comparative Examples

Preparation of Powder Containing Vitamin E

The aim was to divide a small amount of vitamin E into a powder blend. The powder blend consisted of Tapentadol HCl, Polyethylene Oxide 7M, Hydroxypropyl methylcellulose and Polyethylene glycol 6000.

a)) Absorbing Vitamin E on a Solid Carrier

One way of incorporating a small amount of a liquid such as Vitamin E into a powder is first absorbing the liquid to a solid carrier, then blending with the remaining of the solid excipients. If the dilution is important, it can be performed geometrically, e.g. the Vitamin E containing carrier is mixed with one or more solid powder(s) (to obtain a certain dilution) and the blend obtained is diluted again with the same or other solid powder(s).

First it was tried to absorb the vitamin E on one of the excipients, namely polyethylene oxide PEO) 7 M which is a major component of the powder blend. It was tried to coat 1 part of Vitamin E on 9 parts of PEO. Distribution of the Vitamin E onto the PEO 7M was not successful.

b) Therefore, a carrier was introduced, i.e. a powder specifically used for its large surface area so that the amount needed can be as little as possible in order not to interfere too much with the original formulation characteristics.

Neusilin (synthetic amorphous magnesium aluminium metasilicate) was selected as solid carrier for absorption of the Vitamin E due to its high specific surface and proposed chemically inert nature. Two available Neusilin grades (Fuji Chemical Industry Co.), US2 and UFL2, were used to screen absorption capability for the Vitamin E.

The Vitamin E-Neusilin blends were prepared in a Pro-C-epT Mi-Pro lab-scale high shear granulator with a bowl of 250 ml, without heated jacketing and without employing the Mini-Pro's dosing syringe and closed loop system. The Neusilin, Vitamin E and $Fe_2O_3$ were weighed and transferred into the granulation bowl and sheared to the point the product quality did not improve anymore. $Fe_2O_3$ was added in a 1% concentration as a colorant to monitor visually the homogenicity of the blends. The Vitamin E was heated to about 40° C. to reduce viscosity and thus allow better weighing and distribution.

Vitamin E on Neusilin (1:1 w:w)

US2 type Neusilin gave an extremely poor distribution of the Vitamin E with he formation of very large lumps.

Initial aspect of the coated ULF2 was that of successful absorption of the Vitamin onto the Neusilin ULF2, although some small lumps were also present. Over time however the mixture started to agglomerate strongly. Within 1 day, the effect was already pronounced, after several days the agglomeration was such that a large particle sized granulate was formed instead of coated powder.

Because of the clear difference in distribution of Vitamin E with Neusilin grades US2 and UFL2, further experiments to prepare premix and further dilutions were only performed with ULF2.

c) Preparation of a Premix (Dilution of Coated Carrier (Vitamin E on Neusilin) with Further Excipients)

The Vitamin E coated Neusilin ULF2 (1:1 w:w) was sieved through a 75 µm sieve and 1 g of coated carrier was first blended with 24 g of poly(ethylene oxide) (PEO) 7M as inert excipient (=1/25 dilution step) (premix). Next, 2.5 g of this premix was blended again with 47.5 g PEO 7M (=1/20 dilution step) (end mixture) to come to a 1/500 dilution ratio. The blends were prepared using the Turbula mixer.

The aspect of the premix and end mixture was homogenous to the eye. These mixtures were reexamined after more than a week and remained stable whereas the undiluted neusilin-Vitamin E agglomerated completely over time as indicated before. In this experiment, a very fine sieve (75 µm sieve) was used which is not practical on industrial scale.

Vitamin E on Neusilin ULF2 (1:2.5 w:w)

To improve blend quality Neusilin lumps must be avoided. This includes the formation of lumps in the granulator as well as preventing the post-production agglomeration tendency. Therefore the ratio of Neusilin was increased to try to stabilize the carrier/Vitamin E mixture. To help prevent lump formation the Vitamin E was added with a syringe instead of weighed onto the neusilin as a whole. Additionally, the option of immediate dilution of the coated carrier in the PEO was tried. Furthermore the necessity of sieving was evaluated. To this end a single batch of Neusilin was coated, split in 4 fractions, of which 2 were not processed further but one was sieved (500 µm sieve) and 2 fractions were used to produce premixes with again one premix being sieved (coated carrier was sieved over 500 µm sieve (more adapted to production scale compared to 75 µm sieve) and then diluted (1/25 dilution) with PEO).

Heating of Vitamin E (40° C.) was found to be necessary to bring viscosity down enough to allow filling of the syringe. By using the syringe, formation of lumps was greatly reduced since previously Vitamin E could adhere to the granulator walls and thus cause lumps after bowl discharge.

Increasing the amount of Neusilin helped to reduce the degree of agglomerate formation but still did not sufficiently prevent it. When the obtained powder was sieved, it was initially clear of agglomerates but already after one day was no longer distinguishable from the unsieved carrier.

It was seen that the distribution of the Vitamin E in the premix was limited to a crude dispersion of carrier agglomerates. Also the distinction between colored agglomerates and near white PEO slightly increased over time, indicating an unstable system.

Vitamin E on Neusilin ULF2 with EtOH (1:2.5:0.8 w:w):

To further improve the Vitamin E distribution on Neusilin with minimizing aggregate formation, a Vitamin E miscible solvent was selected in order to greatly modify the viscosity of the thick, oily Vitamin E. In this experiment 2.77 g Vitamin E was mixed with 2.22 g Ethanol 96° prior to the filling of the dosing syringe. The mixing took place in the Mi-Pro using a 250 ml bowl. The Vitamin E/ethanol solution was injected in the bowl containing 7.1 g Neusilin UFL2 and ca 100 mg iron oxide. As indicated for the previous experiment, 4 fractions were made from a single coating batch. Two fractions were the unprocessed coated carrier of which only one was sieved through a 500 µm sieve and two fractions were further diluted to premixes with again one being sieved (coated carrier was sieved over 500 µm sieve and then diluted with PEO). The premixes consisted of 1 part coated Neusilin with 19 parts PEO 7M to give a dilution factor of 1/20 for the premix. All fractions were dried overnight at 30° C. under a 250 mbar vacuum.

Using the ethanol, the Vitamin E did not need to be heated anymore to allow filling of the syringe which is considered an advantage since Vitamin E is a strong anti-oxidant, best not exposed too much to heat. Technically the carrier coating can now be done completely without lump formation in the granulation bowl. With time however the undiluted carrier started to agglomerate whether previously sieved or not. The aspect of the premixes looked homogenous under magnification. Post-drying the fractions did not really seem to create additional agglomeration in the samples.

In further experiments it was shown that satisfactory result can also be obtained with less ethanol.

From these experiments it is clear that the carrier system with Vitamin E on Neusilin (synthetic amorphous magnesium aluminium metasilicate) is not stable as such since the finely powdered Neusilin tends to agglomerate strongly over time. The use of ethanol as solvent is beneficial to improve the distribution of the Vitamin E in the powder, even though it is introducing an organic solvent in the manufacturing process which might have detrimental safety implications. In conclusion, the incorporation of Vitamin E in a solid powder by mixing was only possible through the use of a carrier and a solvent as a vehicle. The coated carrier powder obtained was not physically stable and needed to be diluted immediately with a portion of a excipient making up the formulation composition (in the above experiments, a portion of the PEO).

Example 3

Spray Congealing Vitamin E and PEG 6000

PEG 6000 was weighed and molten on an off-line heating plate. Only slightly before the experiments took place an appropriate amount of Vitamin E was added and mechanically mixed with the PEG 6000. The mixture was heated to about 75 to 80° C. and transferred to the spraying nozzle of a Mobile Minor spray dryer by heated feed lines.

The mixture was sprayed through a two-fluid nozzle with $N_2$ pre-heated at 100° C. The cooling gas was also $N_2$ which had an in-let temperature of 11 to 13° C. and out-let temperature in the range of 20-26° C. After spraying the particles were collected in the cyclone of the spray-dryer.

Experiments were conducted with different concentrations of Vitamin E (1%, 2% or 4% (w/w) of actual Vitamin E content. Spray congealing of the Vitamin E with PEG 6000 was successful. The spray congealed product was obtained in a finely powdered state without being sticky or having much agglomeration. Loss of product in the spray chamber was also minimal since high yields were obtained. The aspect of the Vitamin E-PEG was homogenous in color and no brownish zones, indicative of separated Vitamin E, were spotted in the powders or against the chamber walls.

Example 4

Stability Tests

Powders prepared by absorbing vitamin E on a carrier or the powders prepared by spray congealing (prepared according to example 3) were placed in glass bottles and stored under different conditions (5° C. and 30° C./75% Relative Humidity). The concentration of "active" Vitamin E (Vitamin E which still has anti-oxidative activity) was determined by HPLC assay and the appearance of the powders was visually inspected.

The following coated carrier blends were tested:

TABLE 1

Compositions and calculated contents for Neusilin powder 1 and Neusilin powder 2

|  | MATERIAL | QUANTITY (g) | PERCENTAGE |
|---|---|---|---|
| Neusilin powder 1 | | | |
| Carrier | Vitamin E | 4.0 | 30.0% |
| | Ethanol | 1.3 | 10.0% |
| | Neusilin ULF2 | 8.0 | 60.2% |
| Premix | Carrier | 12.0 | 6.7% |
| | PEO 7M | 168.0 | 93.3% |
| Calculated[a] | Vitamin E | 3.60 | 2.0% |
| | Neusilin ULF2 | 7.22 | 4.0% |
| | PEO 7M | 168.0 | 94.0% |
| Neusilin powder 2 | | | |
| Carrier | Vitamin E | 4.0 | 30.0% |
| | Ethanol | 1.3 | 10.0% |
| | Neusilin ULF2 | 8.0 | 60.2% |
| Premix | Carrier | 12.0 | 6.7% |
| | PEO 7M | 168.0 | 93.3% |
| Calculated[b] | Vitamin E | 3.60 | 2.0% |
| | Ethanol | 1.20 | 0.7% |
| | Neusilin ULF2 | 7.22 | 4.0% |
| | PEO 7M | 168.0 | 93.3% |

[a]Calculations assume that all the EtOH has been removed from the mixture.
[b]Calculations assume that the full amount of EtOH is still present in the pre-mix.

The blends were prepared as follows:

In a first process step all the neusilin was coated with the Vitamin E/EtOH mixture in the Mi-Pro (0.25 L bowl, impeller speed 200-400 rpm, chopper speed 500-650 rpm for 45 minutes). After emptying the bowl, fraction 1 was made by blending 5 g of the coated neusilin with 70 g PEO 7M in the Pro-C-epT (12 minutes at 250 rpm impeller speed in the 0.25 L bowl). When this was in turn emptied, fraction 2 was made with 4.5 g coated Neusilin and 63.0 g PEO 7M (16 minutes at 250 rpm impeller speed in the 0.25 L bowl). Fraction 1 and 2 have the same relative compositions but the difference is that fraction 2 (=Neusilin powder 1) was post-dried at 25° C. under a vacuum of 300 mbar for 16 hours, whereas fraction 1 (=Neusilin powder 2) was not.

The neusilin based premixes were found to be unstable. In fact, the Vitamin E content dropped so much already after one month at 30° C./75% RH that the study of those samples was discontinued.

Spray congealed powder prepared as described above (see Example 3) were also subjected to the same conditions. For each Vitamin E concentration (1%, 2% and 4% w/w) a small and a large particle size fraction was tested. Particle size was adjusted by amending the feed rate, nozzle diameter and/or $N_2$ rate during the spray congealing process).

The results are gathered in the below Table 2:

| Condition | | Time | Appearance | Active VitE content (HPLC assay) |
|---|---|---|---|---|
| Spray congealed powder PEG 6000 with 1% w/w Vit E: large particle size (average d50: 73 μm) | 5° C. | Initial | PASS | 97.7 |
| | 5° C. | After 1 month | PASS | 97.2 |
| | | After 3 month | PASS | 95.1 |
| | 30° C./ 75% RH | After 1 month | PASS | 92.1 |
| | | After 3 month | PASS | 82.4 |
| Spray congealed powder PEG 6000 with 1% w/w Vit E: small particle size (average d50: 40 μm) | 5° C. | Initial | PASS | 110.8 |
| | 5° C. | After 1 month | PASS | 110.4 |
| | | After 3 month | PASS | 115.5 |
| | 30° C./ 75% RH | After 1 month | PASS | 103.4 |
| | | After 3 month | PASS | 85.1 |
| Spray congealed powder PEG 6000 with 2% w/w Vit E: large particle size (average d50: 43 μm) | 5° C. | Initial | PASS | 95.1 |
| | 5° C. | After 1 month | PASS | 94.7 |
| | | After 3 month | PASS | 100.8 |
| | 30° C./ 75% RH | After 1 month | PASS | 91.1 |
| | | After 3 month | PASS | 81.1 |
| Spray congealed powder PEG 6000 with 2% w/w Vit E: small particle size (average d50: 12 μm) | 5° C. | Initial | PASS | 82.5 |
| | 5° C. | After 1 month | PASS | 85.2 |
| | | After 3 month | PASS | 86.9 |
| | 30° C./ 75% RH | After 1 month | PASS | 81.9 |
| | | After 3 month | PASS | 85.0 |
| Spray congealed powder PEG 6000 with 5% w/w Vit E: large particle size (average d50: 40 μm) | 5° C. | Initial | PASS | 79.2 |
| | 5° C. | After 1 month | PASS | 78.5 |
| | | After 3 month | PASS | 88.3 |
| | 30° C./ 75% RH | After 1 month | PASS | 76.0 |
| | | After 3 month | PASS | 66.0 |
| Spray congealed powder PEG 6000 with 5% w/w Vit E: small particle size (average d50: 16 μm) | 5° C. | Initial | PASS | 80.2 |
| | 5° C. | After 1 month | PASS | 78.6 |
| | | After 3 month | PASS | 73.2 |
| | 30° C./ 75% RH | After 1 month | PASS | 77.2 |
| | | After 3 month | PASS | 79.3 |

The spray congealed powders showed acceptable stability at 5° C. The samples with 1% Vitamin E seemed a little bit less stable than the other samples which have a higher Vitamin E content. At 30° C./75% RH, the loss of Vitamin E in the spray congealed powders was larger so that cold refrigeration is probably advisable.

Based on the above data it can be seen that the carrier system is not practical to manufacture (use of solvent, need for direct premixing to mitigate physical unstability/demixing) and it is also chemically not stable (Vitamin E assay drops quite rapidly). Spray congealing in the meaning of the present invention highly facilitates the reliable manufacture of powdered systems comprising little amounts of in particular liquids such as vitamin oils into a solid second component, and is looking more promising than the absorption of Vitamin E on carriers.

Example 5

Blend Uniformity (BU)

Powder Blend Composition 1:

| | |
|---|---|
| Tapentadol HCl | 58.24 mg |
| Polyethylene Oxide WSR 303 | |
| Hydroxypropyl methylcellulose | |
| Polyethylene glycol 6000 | |
| Spray congealed powder of Polyethylene glycol 6000 and alpha tocopherol (4.56% of vitamin E in the spray congealed powder) | 13.16 mg |
| Total weight of the powder | 400 mg |

Powder Blend Composition 2:

| | |
|---|---|
| Tapentadol HCl | 291.20 mg |
| Polyethylene Oxide WSR 303 | |
| Hydroxypropyl methylcellulose | |
| Polyethylene glycol 6000 | |
| Spray congealed powder of Polyethylene glycol 6000 and alpha tocopherol (4.56% of vitamin E in the spray congealed powder) | 15.35 mg |
| Total weight of the powder | 700 mg |

Of powder blend composition 1 and 2, batches of 240 kg were prepared.

The spray congealed powder was prepared according to an analoguous process as described in example 3. The individual components of the blend were delumped if necessary (screened using a Sweco separator with 20 mesh or following a passive manual method using a 20 mesh), then weighed and introduced in a 800 L IBC bin. After 20 minutes blending on a Bohle blender at 6 rpm, the bin was opened to take samples from 10 different locations in the bin using a sample thief. The Vitamin E blend uniformity (BU) was determined by determining the active Vitamin E content of the collected samples by HPLC assay and calculating the % relative standard deviation which is a measure of the uniformity of the Vitamin E in the samples.

For blend 1, 3 batches of 240 kg were prepared and the % relative standard deviation for the Vitamin E content for the first batch was 1.5%; for the second batch 2.3% and the third batch 2.9%.

For blend 2, 3 batches of 240 kg were prepared and the % relative standard deviation for the Vitamin E content for the first batch was 2.9%; for the second batch 1.8% and the third batch 1.7%.

These results show good BU.

Example 6

Tablet Content Uniformity (CU)

Powder Blend Composition 3:

| | |
|---|---|
| Tapentadol HCl | 58.24 mg |
| Polyethylene Oxide WSR 303 | |
| Hydroxypropyl methylcellulose | |
| Polyethylene glycol 6000 | |
| Spray congealed powder of Polyethylene glycol 6000 and alpha tocopherol (4% of vitamin E in the spray congealed powder) | 15.00 mg |
| Total weight of the powder | 400 mg |

Powder Blend Composition 4:

| | |
|---|---|
| Tapentadol HCl | 291.20 mg |
| Polyethylene Oxide WSR 303 | |
| Hydroxypropyl methylcellulose | |
| Polyethylene glycol 6000 | |
| Spray congealed powder of Polyethylene glycol 6000 and alpha tocopherol (4% of vitamin E in the spray congealed powder) | 17.50 mg |
| Total weight of the powder | 700 mg |

Powder blends 3 and 4 were prepared as described in example 5. Tablets were prepared from powder blend compositions 3 and 4 as follows. The powder blends were extruded in a co-rotating twin-screw extruder; the resulting strands were cooled and cut into individual pieces which were compressed into tablets of 400 mg (containing 50 mg of tapentadol) respectively 700 mg (containing 250 mg of tapentadol). The collected tablets were film coated in a perforated pan film coater with a suspension consisting of 20% w/w pharmaceutical coating powder in purified water. The coating suspension was applied on the tablet cores to the level of 3% w/w, after which the tablets were dried, and the batch was sampled for analysis.

From 30 tablets prepared from each of the blends, the active Vitamin E content was determined by HPLC assay and the % relative standard deviations was calculated as a measure of content uniformity (CU) of the Vitamin E in the tablets.

The % relative standard deviation for the 400 mg tablets prepared from blend 3 was 4.96% and the % relative standard deviation for the 700 mg tablets prepared from blend 4 was 3.87%.

These results show good CU.

The invention claimed is:
1. Process for preparing a powder comprising the steps of:
   i) providing from 0.1 wt-% to 8 wt-% of at least one first component selected from the group consisting of tocopherol and tocopherol derivatives, said at least one first component:
      being in liquid form at ambient temperature; or
      being a solid or semi-solid at ambient temperature and having an onset of melting in the temperature range from 15° C. to 40° C.,
   ii) providing from 92 wt-% to 99.9 wt-% of at least one second component having a melting point or melting range above ambient temperature and comprising polyalkylene glycol,
   iii) forming a homogenous liquid mixture comprising said at least one first component and said at least one second component by stirring and heating the mixture to or keeping the mixture at a temperature in the range from above the melting point or melting range of said second component to 120° C.,
   iv) transferring the liquid mixture to at least one spray congealing unit by at least one transfer unit, which is adapted to keep the mixture in its liquid form during its transfer, v) spray congealing said mixture, and vi) isolating the powder obtained upon spray congealing.

2. The process according to claim 1, wherein the at least one second component comprises polyethylene glycol.

3. The process according to claim 2, wherein the polyethylene glycol is polyethylene glycol 6000.

4. The process according to claim 1, wherein said transfer unit comprises at least one feed line and at least one pump, wherein at least said feed line is adapted to be heatable.

5. The process according to claim 1, wherein the melting point or melting range of the second component is in the range from >40° C. to 120° C.

6. A powder obtained by the process of claim 1.

7. The powder according to claim 6 having a particle size distribution $d_{50}$ in the range from 40 µm to 300 µm.

8. A solid dosage form formed from the powder of claim 6 and containing at least one pharmaceutically active ingredient.

9. The solid dosage form according to claim 8, wherein said solid dosage form further comprises at least one poly(alkylene oxide), at least one cellulose ether derivative and at least one vitamin oil.

10. The solid dosage form according to claim 9, wherein said vitamin oil is present in an amount of less than 1 wt-%, based on the total weight of the solid dosage form.

11. Process for the preparation of a solid dosage form comprising the steps of a) providing a powder according to the process of claim 1 (component a), b) providing at least one pharmaceutically active ingredient (component b), c) providing at least one third component (component c), d) forming a mixture comprising components a, b and c, e) transforming said mixture into a solid dosage form.

12. The process according to claim 11, wherein said at least one third component (component c) is selected from the group consisting of poly(alkylene oxide), poly(vinyl alcohol), hydroxymethyl cellulose, hydroxyethyl cellulose, hydroxypropyl cellulose, hydroxypropyl methylcellulose and carboxy methylcellulose.

13. The process of claim 11, wherein said step e) of transforming said mixture into a solid dosage form comprises meltextruding said mixture and, f) collecting the extruded product, and g) compressing the extruded product into a tablet.

14. The process according to claim 1, wherein the at least one second component consists of polyethylene glycol.

15. The powder according to claim 6, wherein the at least one second component consists of polyethylene glycol.

16. The powder according to claim 15, wherein the polyethylene glycol is polyethylene glycol 6000.

17. The powder according to claim 6, wherein the first component is tocopherol.

* * * * *